US012735680B2

(12) United States Patent
Suh et al.

(10) Patent No.: US 12,735,680 B2
(45) Date of Patent: Sep. 15, 2026

(54) CELL THERAPEUTIC AGENT FOR CANCER TREATMENT AND COMBINATION THERAPY WITH SAME

(71) Applicant: Cell & Brain Co., Ltd, Jeollabuk-do (KR)

(72) Inventors: Hae Young Suh, Gyeonggi-do (KR); Sung Soo Kim, Seoul (KR); Da Young Chang, Gyeonggi-do (KR); Jin Hwa Jung, Gyeonggi-do (KR); Young Don Lee, Gyeonggi-do (KR); Woo Sup Hwang, Gyeonggi-do (KR); Jin Sung Park, Seoul (KR); Su Jung Lee, Gyeonggi-do (KR)

(73) Assignee: CELL & BRAIN CO., LTD, Jeollabuk-Do (KR)

( * ) Notice: Subject to any disclaimer, the term of this patent is extended or adjusted under 35 U.S.C. 154(b) by 0 days.

(21) Appl. No.: 18/631,774

(22) Filed: Apr. 10, 2024

(65) Prior Publication Data

US 2024/0360417 A1 Oct. 31, 2024

Related U.S. Application Data

(62) Division of application No. 15/554,849, filed as application No. PCT/KR2016/002188 on Mar. 4, 2016, now abandoned.

(30) Foreign Application Priority Data

Mar. 6, 2015 (KR) ........................ 10-2015-0031751

(51) Int. Cl.

| | |
|---|---|
| ***A61K 31/4745*** | (2006.01) |
| ***A61K 31/4188*** | (2006.01) |
| ***A61K 31/506*** | (2006.01) |
| ***A61K 31/513*** | (2006.01) |
| ***A61K 31/675*** | (2006.01) |
| ***A61K 31/704*** | (2006.01) |
| ***A61K 33/243*** | (2019.01) |
| ***A61K 33/244*** | (2019.01) |
| ***A61K 35/12*** | (2015.01) |
| ***A61K 35/28*** | (2015.01) |
| ***A61K 45/06*** | (2006.01) |
| ***C12N 5/0775*** | (2010.01) |

(52) U.S. Cl.

CPC ........ *C12N 5/0665* (2013.01); *A61K 31/4188* (2013.01); *A61K 31/4745* (2013.01); *A61K 31/506* (2013.01); *A61K 31/513* (2013.01); *A61K 31/675* (2013.01); *A61K 31/704* (2013.01); *A61K 33/243* (2019.01); *A61K 33/244* (2019.01); *A61K 35/12* (2013.01); *A61K 35/28* (2013.01); *A61K 45/06* (2013.01); *C12N 5/0663* (2013.01); *C12N 2501/73* (2013.01); *C12N 2510/00* (2013.01); *C12N 2523/00* (2013.01)

(58) Field of Classification Search

CPC ............................ C12N 5/0665; C12N 5/0663; C12N 2501/73; C12N 2510/00; C12N 2523/00; A61K 31/4188; A61K 31/4745; A61K 31/506; A61K 31/513; A61K 31/675; A61K 31/704; A61K 33/243; A61K 33/244; A61K 35/12; A61K 35/28; A61K 45/06; A61P 1/16; A61P 11/00; A61P 13/08; A61P 13/12; A61P 17/00; A61P 1/00; A61P 1/02; A61P 1/04; A61P 1/18; A61P 11/02; A61P 13/10; A61P 15/00; A61P 25/00; A61P 35/00; A61P 35/02; A61P 43/00

See application file for complete search history.

(56) References Cited

U.S. PATENT DOCUMENTS 8,956,862 B2 2/2015 Pal
9,453,202 B2 9/2016 Harman, Jr.

(Continued)

FOREIGN PATENT DOCUMENTS

EP 1906729 B1 * 3/2012 .............. A01N 1/02
JP 2007105037 A 4/2007

(Continued)

OTHER PUBLICATIONS

Liu et al (Stem Cell Research & Therapy (2021) 12:376; Doi: 10.1186/s13287-021-02427-I) (Year: 2021).*

(Continued)

*Primary Examiner* — Peter Paras, Jr.
*Assistant Examiner* — Khoa Nhat Tran
(74) *Attorney, Agent, or Firm* — HULTQUIST, PLLC; Steven J. Hultquist

(57) ABSTRACT

The present disclosure relates to a method for preparing cells for cancer treatment and a kit for cancer treatment comprising cells prepared by the method. The preparation method of the present disclosure can provide F cells, which, in spite of having no difference in the proliferative capacity compared with mesenchymal stem cells expressing cytosine deaminase that are harvested and used immediately after the culture, exhibit a very excellent tumor suppressive effect through the treatment together with 5-FC and induce a remarkable synergistic effect exceeding an effect from combinative treatment with an existing anticancer drug in cases of a combinative treatment with another anticancer drug. Therefore, the present disclosure can be utilized for a kit for cancer treatment comprising such F cells, and thus can be favorably used to maximize the effect of existing cancer treatments.

9 Claims, 10 Drawing Sheets

Specification includes a Sequence Listing.

(56) References Cited

U.S. PATENT DOCUMENTS

| | | | | |
|---|---|---|---|---|
| 2007/0141066 | A1* | 6/2007 | Phillips | G01N 33/57407 435/6.16 |
| 2008/0241115 | A1* | 10/2008 | Suh | A61P 43/00 424/93.21 |
| 2013/0171115 | A1 | 7/2013 | Li et al. | |
| 2014/0065110 | A1 | 3/2014 | Nolta et al. | |
| 2014/0120615 | A1 | 5/2014 | Fong et al. | |
| 2018/0037869 | A1 | 2/2018 | Suh et al. | |

FOREIGN PATENT DOCUMENTS

| | | | |
|---|---|---|---|
| JP | 2008545755 | A | 12/2008 |
| JP | 2009510052 | A | 3/2009 |
| JP | 2010537973 | A | 12/2010 |
| KR | 10-2009-0023070 | A | 3/2009 |
| KR | 10-1022401 | B1 | 3/2011 |
| KR | 10-2013-0109417 | A | 10/2013 |
| WO | WO2006130812 | A2 | 12/2006 |
| WO | WO2007037653 | A1 | 4/2007 |
| WO | 2008019148 | A2 | 2/2008 |
| WO | WO2009028870 | A2 | 3/2009 |
| WO | 2011101834 | A1 | 8/2011 |

OTHER PUBLICATIONS

Tomov (Neural Regen Res 15(7):1173-1178. doi: 10.4103/1673-5374.270296, Jan. 9, 2020) (Year: 2020).*

Caplan et al (Front. Immunol. 10:1645, doi: 10.3389/fimmu.2019.01645, published Jul. 31, 2019) (Year: 2019).*

Lin et al (Mater. Adv., 2021, 2, 2561-2583, DOI: 10.1039/d0ma00732c) (Year: 2021).*

Liu et al (Front. Cell. Neurosci. 15:637210. Doi: 10.3389/fncel.2021.637210) (Year: 2021).*

Huang et al (Cancer Gene Therapy (2013) 20, 544-551; doi:10.1038/cgt.2013.51; published online Aug. 23, 2013) (Year: 2013).*

Serrano et al (Molecular Oncology 13 (2019) 579-590, doi:10.1002/1878-0261.12461) (Year: 2019).*

Bonomi, A., et al., "Human CD14+ cells loaded with Paclitaxel inhibit in vitro cell proliferation of glioblastoma", Cytotherapy, 2015, pp. 310-319, vol. 17, Publisher: International Society for Cellular Therapy.

Brown, A. B., et al., "Intravascular Delivery of Neural Stem Cell Lines to Target Intracranial and Extracranial Tumors of Neural and Non-Neural Origin", Human Gene Therapy, Dec. 10, 2003, pp. 1777-1785, vol. 14.

Chang, D., et al., "The Growth of Brain Tumors Can Be Suppressed by Multiple Transplantation of Mesenchymal Stem Cells Expressing Cytosine Deaminase", Int. J. Cancer, 2010, pp. 1975-1983, vol. 127.

Chung, T., et al., "Monitoring the Effect of Mesenchymal Stem Cell Therapy Using Cytosine Deaminase-Expressing MSC and 5-FC Prodrug by PET/MR/BLI in Orthotopic Glioma Model", www.wmis.org/abstracts/2013/data/papers/SS120.htm, Sep. 21, 2013, Presentation No. SS 120—Abstract.

Douillard, Jy, et al., "Irinotecan combined with fluorouacil compared with fluorouacil alone as first-line treatment for metastatic colorectal cancer: a multicentre randomised trial", The Lancet, 2000, pp. 1041-1047, vol. 355.

Fan, C., et al., "The Potentials of Human Adipose Tissue Derived Mesenchymal Stem Cells in Targeted Therapy of Experimental Glioma", Chin J. Contemp Neurol Neurosurg., Dec. 2016, pp. 651-654, vol. 12, No. 6.

Feng, Z., et al., "Fresh and Cryopreserved, Uncultured Adipose Tissue-Derived Stem and Regenerative Cells Ameliorate Ischemia-Reperfusion-Induced Acute Kidney Injury", Nephrol Dial Transplant, 2010, pp. 3874-3884, vol. 25.

Francois, M., et al., "Cryopreserved Mesenchymal Stromal Cells Display Impaired Immunosuppressive Properties as a Result of Heat-Shock Response and Impaired Interferon-gamma Licensing", Cytotherapy, 2012, pp. 147-152, vol. 14.

Galipeau, J., "The Mesenchymal Stromal Cells Dilemma—Does a Negative Phase III Trial of Random Donor Mesenchymal Stromal Cells in Steroid-Resistant Graft-Versus-Host Disease Represent a Death Knell or a Bump in the Road?", Cytotherapy, 2013, pp. 2-8, vol. 15.

Huang, TT, et al., "Toca 511 gene transfer and 5-fluorocytosine in combination with temozolomide demonstrates synergistic therapeutic efficacy in a temozolomide-sensitive glioblastoma model", Cancer Gene Therapy, 2013, pp. 544-551, vol. 20, Publisher: Nature America, Inc.

Jang, M., et al., "Cancer Cell Metabolism: Implications for Therapeutic Targets", Experimental and Molecular Medicine, 2013, pp. 1-9, vol. 45.

Jung, J., et al., "Three-Dimensional Assessment of Bystander Effects of Mesenchymal Stem Cells Carrying a Cytosine Deaminase Gene on Glioma Cells", Am J. Cancer Research, 2015, pp. 2686-2696, vol. 5, No. 9.

Kucerova, L., et al., "Increased Proliferation and Chemosensitivity of Human Mesenchymal Stromal Cells Expressing Fusion Yeast Cytosine Deaminase", Stem Cell Research, 2012, pp. 247-258, vol. 8.

Mata, M., et al., "Effects of cryopreservation on effector cells for antibody dependent cell-mediated cytotoxicity (ADCC) and natural killer (NK) cell activity in 51cR-releaseand CD107a assays", Journal of Immunological Methods, Jan. 20, 2014, pp. 1-9, vol. 406, Publisher: Elsevier B.V.

Nouri, F.S., et al., "Genetically Engineered Theranostic Mesenchymal Stem Cells for the Evaluation of the Anticancer Efficacy of Enzyme/Prodrug Systems", Journal of Controlled Release, 2015, pp. 179-187, vol. 200.

Park, B., et al., "Hematopoietic Stem Cell Expansion and Generation: the Ways to Make a Breakthrough", Blood Research, Dec. 2015, pp. 194-203, vol. 50, No. 4.

Park, J.S., et al., "Retrovirus-mediated transduction of a cytosine deaminase gene preserves the stemness of mesenchymal stem cells", Experimental & Molecular Medicine, 2013, pp. 1-9, vol. 45, No. 10.1038/emm.2013.21, Publisher: www.nature.com/emm.

Pittenger, M.F., "Mesenchymal Stem Cells From Adult Bone Marrow", Methods in Molecular Biology, 2008, pp. 27-44, vol. 449.

Pollock, K., et al., "Clinical Mesenchymal Stromal Cell Products Undergo Functional Changes in Response to Freezing", Cytotherapy, 2015, pp. 38-45, vol. 17.

Qazi, B., et al., "Recent Advances in Underlying Pathologies Provide Insight into Interleukin-8 Expression-Mediated Inflammation and Angiogenesis", International Journal of Inflammation, Dec. 22, 2011, pp. 1-24, vol. 2011; 2011:908468, No. 10.4061/2011/908468.

Sohni, A., et al., "Mesenchymal Stem Cells Migration Homing and Tracking", Stem Cells Internationl, Epub Sep. 30, 2013, pp. 1-14, vol. 2013; 2013: 130763, No. 10.1155/2013/130763.

Tomayko, M., et al., "Determination of subcutaneous tumor size in athymic (nude) mice", Cancer Chemotherapy and Pharmacology, 1989, pp. 148-154, vol. 24, Publisher: Springer-Verlag.

Walasek, M.A., et al., "Hematopoietic Stem Cell Expansion: Challenges and Opportunities", Annlas of the New York Academy of Sciences, 2012, pp. 138-150, vol. 1266.

Wick, A., et al., "Rechallenge with temozolomide in patients with recurrent gliomas", J. Neurol, 2009, pp. 734-741, vol. 256, Publisher: Springer.

Wu, C-H, et al., "Transfection of mouse bone marrow mesenchymal stem cells with liposome mediated cytosine deaminase genes", Journal of Clinical Rehabilitive Tissue Enginnering Research, Jan. 1, 2009, pp. 133-136, vol. 13, No. 1.

NCI Dictionary of Cancer Terms, Definition of 5-fluorouracil, https://www.cancer.gov/publications/dictionaries/cancer-terms/def/5-fluorouracil, 2022, NIH National Cancer Institute.

* cited by examiner (A)

(B)

(A)

(B)

(C)

(A)

(B)

(C)

SEQUENCE LISTING

```
Sequence total quantity: 2
SEQ ID NO: 1            moltype = DNA  length = 40
FEATURE                 Location/Qualifiers
source                  1..40
                        mol_type = other DNA
                        organism = synthetic construct
SEQUENCE: 1
gaattcaggc tagcaatgtc tcgaataacg ctttacaaac                    40

SEQ ID NO: 2            moltype = DNA  length = 26
FEATURE                 Location/Qualifiers
source                  1..26
                        mol_type = other DNA
                        organism = synthetic construct
SEQUENCE: 2
ggattctcta gctggcagac agccgc                                   26
```

CELL THERAPEUTIC AGENT FOR CANCER TREATMENT AND COMBINATION THERAPY WITH SAME

CROSS-REFERENCE TO RELATED APPLICATIONS

This is a divisional under 35 USC § 120 of U.S. patent application Ser. No. 15/554,849 filed Aug. 31, 2017 for CELL THERAPEUTIC AGENT FOR CANCER TREATMENT AND COMBINATION THERAPY WITH SAME, which in turn is a U.S. national phase under 35 USC § 371 of International Patent Application No. PCT/KR2016/002188 filed Mar. 4, 2016, which in turn claims priority under 35 USC § 119 of Korean Patent Application No. 10-2015-0031751 filed Mar. 6, 2015. The disclosures of all such applications are hereby incorporated herein by reference in their respective entireties, for all purposes.

REFERENCE TO SEQUENCE LISTING

This application includes an electronically submitted sequence listing in .xml format. The .xml file contains a sequence listing entitled "400DIV_SeqListing.xml" created on Jul. 15, 2024 and is 2,897 bytes in size. The sequence listing contained in this .xml file is part of the specification and is hereby incorporated by reference herein in its entirety.

TECHNICAL FIELD

The present disclosure relates to a method for preparing cells for cancer treatment, an adjuvant for anti-cancer comprising cells prepared by the same, a kit for cancer treatment, and a method for cancer treatment.

BACKGROUND ART

Millions of people around the world die from various types of cancer including bone cancer, bladder cancer, blood cancer (leukemia), brain cancer, breast cancer, colorectal cancer, cervical cancer, esophageal cancer, bowel cancer, kidney cancer, lung cancer, liver cancer, oral cancer, nasal cancer, neural cancer, ovarian cancer, pancreatic cancer, skin cancer, stomach cancer, prostate cancer, neck cancer, uterine cancer, and vaginal cancer. Over the years, several methods including radiation and chemotherapy have been used to treat cancer, but the number of cancer patients is still increasing. It has been widely reported that radiation and chemotherapy may cause toxicity related diseases and even some patients die. In addition, in the case of specific cancer, there is a problem in that malignant cells remain difficult to treat. As a result, it is required to extensively study physiology or phenotype of cancer cells to find a treatment method that selectively kills the cancer cells without causing adverse effects on the patient's healthy cells.

In particular, a brain tumor is a type of cancer that causes great damage to the brain and has a very low survival rate. Among conventional treatment methods for the brain tumor, extraction by surgical operation is the most effective treatment, but there are a number of cases in that the surgery is not possible depending on the type and location of the brain tumor, and the risk of postoperative complications is very high at the time of complete extraction. Further, since a brain-blood barrier (BBB) that inhibits drug penetration is present in the brain, in order to treat brain tumor by chemotherapy using an anti-cancer agent, it is required to administer a high concentration of anti-cancer agent as compared to other types of cancer, which causes serious side effects in other organs of the body. Therefore, there is a need for a novel adjuvant method, a therapeutic agent, and an adjuvant that are able to lower the dose of the anti-cancer agent by enhancing effects of the anti-cancer agent.

In addition, a gene therapy method is a method of directly introducing a gene that inhibits proliferation of cancer cells into the cancer cells. For gene introduction, a virus is mainly used, but since the virus itself does not have an ability to move to cancer, it is required to inject the virus surgically. However, it is practically impossible to inject the viruses into every microscopic tumor or cancer cells, and thus, there is a limitation in targeting the cancer cells.

In this connection, Korean Patent Registration No. 10-1022401 is known as a method for introducing a suicide gene into a mesenchymal stem cell to enhance targeting and treat cancer. However, KR 10-1022401 does not disclose a combination therapy adjuvant for improving an effect of an anti-cancer agent by manipulating the mesenchymal stem cell in a special environment and administering the mesenchymal stem cell in combination with another anti-cancer agent, and does not disclose a method for periodic administration.

Further, recently, a number of studies on combination therapies such as combination therapy of two or more kinds of anti-cancer agents have been conducted. In this regard, not only a combination therapy of a chemotherapeutic agent, but also a combination therapy of a chemotherapeutic agent in combination with different kinds of anti-cancer therapies, etc., has been recently reported. However, in the case of combination therapy, there are many cases in which combination administration of each drug shows a simple additive effect of the same degree of drug efficacy. Further, unpredictable side effects have been reported, for example, an effect of the drugs is rather deteriorated by an interaction of the drugs, etc. Thus, studies on the combination administration of drugs are still continuing.

In connection with the combination administration in cancer, there is also a study on the combination therapy of chemotherapeutic agents and cell therapeutic agents, such as mesenchymal stem cells. However, in the combination therapy using the mesenchymal stem cells, researches aiming at administration of cells such as autologous stem cells for recovery of cells damaged after anti-cancer therapy by chemotherapeutic agents have been intensively conducted, and there are not many attempts to utilize the stem cells themselves as therapeutic agents for combination therapy.

Therefore, there is a need to develop a therapeutic agent and a treatment method capable of having high targeting so that cancer or tumor therapeutic agents are able to be accurately transferred to a cancer tissue, being non-toxic so as not to affect parts other than the tumor, and being repeatedly administered until cancer is eliminated because of no immunotoxicity. Further, there is a need and requirement for a novel therapeutic method, therapeutic agent, therapeutic adjuvant and combination therapy that are able to improve or enhance the efficacy of existing anti-cancer agents.

DISCLOSURE

Technical Problem

The present inventors studied a novel cancer therapeutic agent that is capable of overcoming the limitations of the existing chemotherapy, found that cells prepared by introducing a cytosine deaminase gene into a mesenchymal stem cell to prepare mesenchymal stem cell/cytosine deaminase (MSC/CD), followed by freezing and thawing, could exhibit very excellent tumor suppressive effect and survival rate improvement effect as compared to simply cultivated MSC/CD cells, and maximize effects of combination therapy with existing anti-cancer agents, and completed the present disclosure.

An object of the present disclosure is to provide a method for preparing "F cells" which are cells usable as an adjuvant for cancer treatment, a kit for cancer treatment comprising F cells, a combined administration agent with the F cells and a chemotherapeutic agent, and a combined administration method.

Technical Solution

In order to achieve the foregoing objects, the present disclosure provides a method for preparing F cells comprising: 1) introducing cytosine deaminase (CD) into a mesenchymal stem cell (MSC) to prepare mesenchymal stem cell/cytosine deaminase (MSC/CD); 2) freezing the prepared MSC/CD to prepare frozen MSC/CD; and 3) thawing and suspending the frozen MSC/CD to prepare F cells.

In addition, the present disclosure provides an adjuvant for anti-cancer comprising the F cells prepared by the method.

Further, the present disclosure provides a kit for cancer treatment comprising the F cells prepared by the method, and 5-fluorocytosine (5-FC).

In addition, the present disclosure provides a method for preventing or treating cancer comprising: 1) introducing cytosine deaminase (CD) into a mesenchymal stem cell (MSC) to prepare mesenchymal stem cell/cytosine deaminase (MSC/CD); 2) freezing the prepared MSC/CD to prepare frozen MSC/CD; 3) thawing and suspending the frozen MSC/CD to prepare F cells; 4) administering the F cells to a subject in need of treatment; and 5) administering 5-fluorocytosine (5-FC) to a subject in need of treatment.

Advantageous Effects

According to the preparation method of the present disclosure, it is possible to provide the F cells, in spite of having no difference in the proliferative capacity compared with mesenchymal stem cells expressing cytosine deaminase, which are harvested and used immediately after culturing, exhibit a very excellent tumor suppressive effect through the treatment together with 5-FC, and induce a remarkable synergistic effect exceeding an effect from combination therapy with an existing anti-cancer agent, even in cases of a combination therapy with another anti-cancer agent. Therefore, the present disclosure may be utilized as a kit for cancer treatment comprising such F cells, and thus may be favorably used to maximize the effect of existing cancer treatments.

BEST MODE

Figure 1:
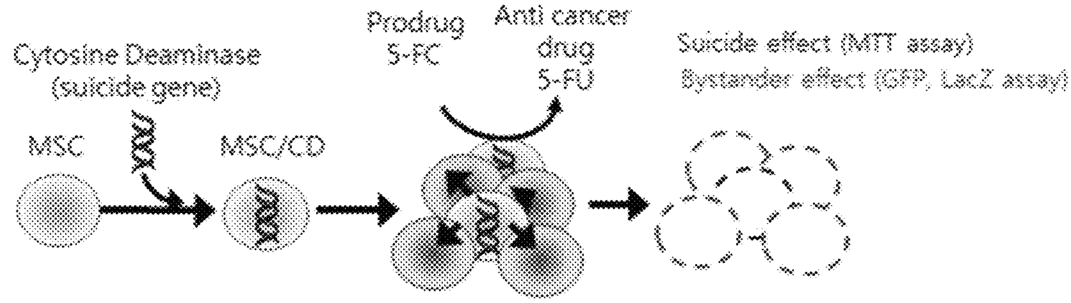
FIG. 1 is a schematic diagram of a mesenchymal stem cell line (MSC/CD) that stably expresses cytosine deaminase, a suicide effect thereof, and a bystander effect.

The present disclosure provides a method for preparing F cells including: 1) introducing cytosine deaminase (CD) into a mesenchymal stem cell (MSC) to prepare mesenchymal stem cell/cytosine deaminase (MSC/CD); 2) freezing the prepared MSC/CD to prepare frozen MSC/CD; and 3) thawing and suspending the frozen MSC/CD to prepare F cells.

According to the method for preparing F cells of the present disclosure, it is possible to provide the F cells, in spite of having no difference in the proliferative capacity compared with mesenchymal stem cells expressing cytosine deaminase, which are harvested and used immediately after culturing I cells, exhibit a very excellent tumor suppressive effect when treated with 5-FC, and induce a remarkable synergistic effect exceeding an effect from combination therapy with an existing anti-cancer agent, even in cases of a combination therapy with another anti-cancer agent.

The "MSC/CD" used herein refers to a mesenchymal stem cell prepared to express cytosine deaminase (CD) in the mesenchymal stem cell. The mesenchymal stem cell into which the cytosine deaminase is introduced refers to a cell that moves to the vicinity of cancer cells with a tropism towards the cancer cells, and continuously expresses cytosine deaminase to induce suicide effect itself, and converts a non-toxic prodrug into an active anti-cancer agent to exhibit a bystander effect in which surrounding cancer cells are killed. The MSC/CD is advantageous in that since it undergo cell death, side effects that may be caused by undesired continuous effects may be reduced, and since it moves to the vicinity of cancer cells, infiltrative cancer cells may be killed, thereby acting as an effective anti-cancer agent. In particular, the "F cell", which is a cell prepared by freezing/thawing the MSC/CD, exhibits synergistic effect in which an anti-cancer effect is significantly increased when used in combination with the existing anti-cancer agent, thereby being utilized as an adjuvant enhancing the effect of the anti-cancer agent.

The term "mesenchymal stem cell (MSC)" of the present disclosure is a kind of stem cells that are able to be collected from bone marrow and umbilical cord blood, and is referred to a multipotent stromal cell that is capable of proliferation, and in particular, that is capable of being differentiated into various types of cells such as bone cells, cartilage cells, muscle cells, and fat cells, unlike hematopoietic stem cells. Therefore, the mesenchymal stem cell of the present disclosure may preferably be the multipotent mesenchymal stem cell.

Term "cytosine deaminase" of the present disclosure is a suicide gene, which functions to convert a prodrug harmless to the human body into a cytotoxic anticancer material, and specifically, a gene that converts 5-fluorocytosine (5-FC) which is a prodrug of 5-fluorouracil (5-FU), into 5-FU.

The suicide gene may be introduced into the mesenchymal stem cell according to methods for intracellular introduction of genes known in the art, such as a method of using a non-viral vector or a virus vector including the same, or a physical method. Examples of such physical methods for gene transfer may include electroporation, hydroporation, injection, etc. Examples of gene transfer using non-viral vectors may include methods of using cationic lipids, lipid polymers, or nanoparticles. The viral vector may include, without limitation, a replicable viral vector, a non-replicable viral vector, such as an adenoviral vector, an adeno-associated viral vector, a retroviral vector, herpes simplex virus, a hybrid adenoviral system, pox virus, a lentivirus vector, and Epstein Barr virus.

For example, in an exemplary embodiment of the present disclosure, the suicide gene may be introduced into the retrovirus vector to construct an expression vector, the vector may be transfected into packaging cells, the transfected packaging cells may be cultured and filtered to obtain a retrovirus solution, and this retrovirus solution may be used to transfect the mesenchymal stem cell, thereby inserting the suicide gene into the mesenchymal stem cell. Next, the mesenchymal stem cell that continuously expresses the suicide gene may be obtained using a selection marker included in the retrovirus vector.

In addition, since mesenchymal stem cell is known to have low immunorejection even during allotransplantation, it is possible to use either cells isolated from others or cells collected from patients with cancer themselves, and to further minimize immunorejection among individuals through separation from bone marrow having similar HLA (human leukocyte antigen) types using a database of blood banks.

The MSC/CD of the present disclosure may be obtained by introducing a suicide gene into the isolated stem cell at first, followed by screening, proliferation and differentiation under an appropriate condition in a test tube, or may be obtained by sufficiently proliferating the stem cell, introducing a suicide gene into the stem cell, followed by differentiation into the mesenchymal stem cell. The MSC/CD is injected into a subject in need of treatment by the presence of the suicide gene, and kills themselves after, for example, 2 to 30 days, preferably 5 to 15 days, more preferably 5 to 10 days, but is not limited thereto, from the injection, thereby reducing side effects that may be induced by continuous action.

Term "F cell (frozen cell)" of the present disclosure refers to a cell that is not undergone an additional culturing step, free of culturing F cells, after freezing and thawing the MSC/CD, which is the mesenchymal stem cell into which the cytosine deaminase (CD) is introduced, and is defined as a cell being thawed and suspended, or suspended and washed with a purpose of administration of cells to the subject to be treated. More specifically; the F cell refers to a cell obtained by introducing cytosine deaminase (CD) into the mesenchymal stem cell to prepare the MSC/CD, culturing, freezing the cell in a freezing medium, thawing the cell at room temperature immediately before use, followed by suspension, for example, in a Plasma Solution A, or the like, containing human serum albumin, which is not limited thereto, and centrifugation. As a cell differentiated from the F cell of the present disclosure, an immediately harvested cell (I cell)" may be exemplified, which is obtained by performing the same freezing and thawing step on the MSC/CD, but maximizing the concentration and activity through the subsequent culturing process, and is used by directly harvesting the cell in the culture.

The F cell, compared to the I cell, of the present disclosure is characterized in that the anti-cancer effect is increased without culturing step, which is performed generally to maximize activation and without increasing a colony forming ability. In addition, the F cell of the present disclosure may have an advantage of being immediately administered to a patient in need of treatment together with the improvement of the anti-cancer effect.

In the present disclosure, the cells in a cryopreserved state or frozen state may be stored by using any means known in the art for maintaining the cells to be in frozen state, such as a freezing preservation liquid, a freezing medium, etc. For example, the means may include media including freezing protectants such as dimethylsulfoxide (DMSO), dextran, human serum, human serum albumin, bovine serum, bovine serum albumin, poly-1-lysine, polyvinylpyrrolidone, hydroxy-ethyl-starch, ethylene glycol, polyethylene glycol, glycerol, and percoll (for example, cryostor CS2, cryostor CS10 commercially available from BioLife Solutions Inc.), and specifically, cryostor CS2, cryostor CS10, and 2 to 10% DMSO medium, and more specifically, 2, 5, and 10% DMSO media, etc.

The F cell of the present disclosure exhibits in vitro colony forming ability similar to that of the I cell, and also effectively exhibits the bystander effect of the MSC/CD. Further, the F cell exhibits an inhibitory effect in vivo on a variety of tumors including brain tumors and subcutaneous tumors twice or higher as compared to the I cell or the control group, and exhibits a highly elevated anti-cancer effect in the combination therapy with temozolomide (TMZ)

which is the existing anti-cancer agent. In other words, even though the F cell has no difference in the colony forming ability as compared to the I cell, the F cell exhibits a remarkable anti-cancer effect that are not able to be expected in vitro and an effect as an anti-cancer agent adjuvant, as compared to other I cells, due to the intrinsic activity of the F cell given according to the preparation method.

That is, the F cells of the present disclosure may be differentiated from I cells that are conventionally used, by preparation methods in which cell culturing is not further performed after freezing.

Therefore, the present disclosure provides the method for preparing F cells characterized in that the F cells are not subjected to cell culturing after freezing.

The F cell of the present disclosure is a cell for cancer treatment that is usable for cancer treatment. The F cells may be used to treat, without limitation, all carcinomas capable of being extracted as cancer and carcinoma, and may be administered to a subject in need of treatment before, simultaneously with, and after chemotherapy using administration of anti-cancer agent.

The cancer may be, for example, at least one selected from the group consisting of squamous cell cancer (for example, squamous cell cancer of epithelium), small cell lung cancer, non-small cell lung cancer, lung cancer, peritoneal cancer, colorectal cancer, biliary tumor, nasopharyngeal cancer, laryngeal cancer, bronchial cancer, oral cancer, osteosarcoma, gallbladder cancer, kidney cancer, leukemia, bladder cancer, melanoma, brain cancer, glioma, brain tumor, skin cancer, pancreatic cancer, breast cancer, liver cancer, bone cancer, esophageal cancer, colon cancer, gastric cancer, cervical cancer, prostate cancer, ovarian cancer, head and neck cancer, and rectal cancer, and more preferably, brain tumor, pancreatic cancer, liver cancer, lung cancer, colon cancer, and skin cancer.

Further, the F cell of the present disclosure may also be an adjuvant for anti-cancer. The adjuvant for anti-cancer refers to an adjuvant that is capable of inducing faster action of a primary therapy and strongly forming an anti-cancer action thereof by combination therapy with the primary therapy, for example, cancer treatment by chemical therapy or surgical operation. The adjuvant for anti-cancer may be used to enhance the effect of anti-cancer agent, which is a main therapeutic agent primarily used in chemotherapy using the anti-cancer agent, and may be used to maximize cancer treatment effect by treating residual cancer cells after surgery.

The F cells may be present in a form of a composition for use in cancer therapy or for use in the adjuvant for anti-cancer, and such a composition may include pharmaceutically acceptable excipients, carriers and diluents. A particularly preferred injection form is preferably formulated into an injection form suitable for injection into a tissue or organ.

Accordingly, the present disclosure provides an adjuvant for anti-cancer including the F cells.

The F cell may be injected into the patient's body according to the physician's prescription or by a method well known in the art, and a single dose will be determined in consideration of various related factors such as a disease to be treated, the severity of the disease, the route of administration, the body weight, age, and sex of the patient, etc.

Further, the present disclosure provides a kit for cancer treatment including the F cells, and 5-fluorocytosine (5-FC).

The kit for cancer treatment is prepared for the purpose of the combination therapy of F cells and 5-fluorocytosine (5-FC), and means a kit prepared so that the F cells are able to be injected before, simultaneously with, and after administration of 5-fluorocytosine (5-FC) which is a prodrug, to a subject in need of treatment.

The kit for cancer treatment may comprise a first compartment and a second compartment, wherein the first compartment may comprise the F cells for cancer treatment or the F cells acting as an adjuvant for anti-cancer, and the second compartment may include 5-fluorocytosine (5-FC). The kit may be contained in one container or in several different small containers with each divided dosage in order to improve convenience and portability. Therefore, several containers may exist in each container according to an arrangement method. The kit of the present disclosure may include, if necessary, equipment necessary for use, instructions including descriptions of administration methods for each component, etc.

In addition, a kit for cancer treatment of the present disclosure may further include an anti-cancer agent. The anti-cancer agent may include, but is not limited to, anti-cancer agents known in the art, and preferably may be at least one selected from the group consisting of nitrogen mustard, imatinib, oxaliplatin, rituximab, elotinib, trastuzumab, gefitinib, bortezomib, sunitinib, carboplatin, sorafenib, bevacizumab, cetuximab, viscum album, asparaginase, tretinoin, hydroxycarbamide, dasatinib, estramustine, gemtuzumab ozogamicin, ibritumomab tiuxetan, heptaplatin, methylaminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacytidine, cytarabine, fludarabine, enocitabine, decitabine, mercaptopurine, thioguanine, cladribine, carmofur, raltitrexed, docetaxel, paclitaxel, belotecan, topotecan, vinorelbine, etoposide, vincristine, vinblastine, tenifocide, idarubicin, epirubicin, mitoxantrone, mitomycin, bleomycin, daunorubicin, dactinomycin, pirarubicin, aclarubicin, pepromycin, temozolomide, busulfan, ifosfamide, cyclophosphamide, melphalan, altretamine, dacarbazine, thiotepa, nimustine, chlorambucil, mitolactol, taxotere, gleevec, taxol, herceptin, tarceva, avastin, zoladex, adriamycin, irinotecan, 10058-F4, cisplatin, cyclophosphamid, nitrosourea-based anti-cancer agent, methotrexate, and doxorubicin. The nitrosourea includes carmustine, lomustine, and the like. The anti-cancer agent may be included in the third compartment of the kit for cancer treatment.

In addition, the present disclosure provides a method for preventing or treating cancer including: 1) introducing cytosine deaminase (CD) into a mesenchymal stem cell (MSC) to prepare mesenchymal stem cell/cytosine deaminase (MSC/CD); 2) freezing the prepared MSC/CD to prepare frozen MSC/CD; 3) thawing and suspending the frozen MSC/CD to prepare F cells; 4) administering the F cells to a subject in need of treatment; and 5) administering 5-fluorocytosine (5-FC) to a subject in need of treatment.

The subject is preferably a mammal, including a human, and may include all of a patient in need of cancer treatment, a patient undergoing cancer treatment, a patient experienced with cancer treatment, and a patient who need to be treated for cancer, and may also include a patient who underwent surgery to extract the cancer for cancer treatment.

Further, the present disclosure provides the method for preventing or treating cancer, further including: 6) administering an anti-cancer agent to a subject in need of treatment.

Further, the present disclosure provides a method for preventing or treating cancer including: 4) administering an anti-cancer agent to a subject in need of treatment before, simultaneously with administration of the F cells of step 4).

That is, the present disclosure provides the method for preventing or treating cancer including both of simultaneous administration of the F cells and the anti-cancer agent to a subject in need of treatment, and sequential administration, such as administration of the anti-cancer agent after administration of the F cells, and administration of the F cells after administration of the anti-cancer agent to a subject in need of treatment.

The anti-cancer agent may include, but is not limited to, anti-cancer agents known in the art, and preferably may be at least one selected from the group consisting of nitrogen mustard, imatinib, oxaliplatin, rituximab, elotinib, trastuzumab, gefitinib, bortezomib, sunitinib, carboplatin, sorafenib, bevacizumab, cetuximab, viscum album, asparaginase, tretinoin, hydroxycarbamide, dasatinib, estramustine, gemtuzumab ozogamicin, ibritumomab tiuxetan, heptaplatin, methylaminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacytidine, cytarabine, fludarabine, enocitabine, decitabine, mercaptopurine, thioguanine, cladribine, carmofur, raltitrexed, docetaxel, paclitaxel, belotecan, topotecan, vinorelbine, etoposide, vincristine, vinblastine, tenifocide, idarubicin, epirubicin, mitoxantrone, mitomycin, bleomycin, daunorubicin, dactinomycin, pirarubicin, aclarubicin, pepromycin, temozolomide, busulfan, ifosfamide, cyclophosphamide, melphalan, altretamine, dacarbazine, thiotepa, nimustine, chlorambucil, mitolactol, taxotere, gleevec, taxol, herceptin, tarceva, avastin, zoladex, adriamycin, irinotecan, 10058-F4, cisplatin, cyclophosphamid, nitrosourea-based anti-cancer agent, methotrexate, and doxorubicin. The nitrosourea includes carmustine (BCNU), lomustine (CCNU), etc. The anti-cancer agent may be appropriately and selectively prescribed according to a prescription dose of the anticancer agent which is widely known in the art, but may be prescribed at a dose smaller than an average prescription dose in consideration of the synergistic effect with the F cells of the present disclosure.

The F cell of the present disclosure and 5-fluorocytosine may be administered simultaneously or sequentially with time differences, which may be selected depending on appropriate time and period for conversion of 5-fluorocytosine to 5-fluorouracil by the F cell.

Therefore, the present disclosure provides the method for preventing or treating cancer characterized in that the F cells of step 4) and the 5-fluorocytosine of step 5) are administered simultaneously or sequentially.

Further, the anti-cancer agent used in combination with the 5-fluorocytosine of the present disclosure may be administered simultaneously or sequentially with time differences, and may be selected according to appropriate time and period.

Therefore, the present disclosure provides the method for preventing or treating cancer characterized in that the 5-fluorocytosine of step 5) and the anti-cancer agent of step 6) are administered simultaneously or sequentially.

The sequential administration in the present disclosure means that multiple components to be administered are administered to a subject with time differences, and the order of each of active components may be appropriately adjusted.

The F cells may be delivered in a pharmaceutically effective amount to a tumor site of the subject, and the delivery is preferably performed by an injection form, but is not limited thereto. In particular, it is more preferable that the injection is administered for mammals, preferably a human patient.

The F cells are the MSC/CD cells that are immediately used by freezing, thawing, or thawing and washing, and have a cytotoxic effect, which may be killed in a subject body for a predetermined period of time by a suicide effect, preferably 5 to 15 days after injection. Thus, the F cells may be repeatedly administered for continuous treatment. Further, the 5-FC, the anti-cancer agent may be repeatedly administered depending on the therapeutic purpose and the condition of the patient. The cycle of the repeated administration of the F cells, 5-FC, and the anti-cancer agent may be appropriately adjusted according to the therapeutic condition of the patient, and the cycle may be preferably every 10 to 30 days. For example, in consideration of the cell death of the MSC/CD, the repeated administration is preferable after at least 10 days, and the repeated administration every 30 days is also preferable considering that the cells are injected with a syringe.

Therefore, the present disclosure provides the method for preventing or treating cancer characterized in that the administration of the F cells of step 4) is repeated every 10 to 30 days.

Depending on the repetition of the F cell administration cycle, the 5-fluorocytosine may also be repeatedly administered periodically, and optionally, the anti-cancer agent for combined administration may also be repeatedly administered periodically.

In the method for preventing or treating cancer of the present disclosure, F cells may be used to treat, without limitation, all carcinomas capable of being extracted as cancer and carcinoma, and may be administered to a subject in need of treatment before, simultaneously with, and after chemotherapy using administration of anti-cancer agent. The cancer may be, for example, at least one selected from the group consisting of squamous cell cancer (for example, squamous cell cancer of epithelium), small cell lung cancer, non-small cell lung cancer, lung cancer, peritoneal cancer, colorectal cancer, biliary tumor, nasopharyngeal cancer, laryngeal cancer, bronchial cancer, oral cancer, osteosarcoma, gallbladder cancer, kidney cancer, leukemia, bladder cancer, melanoma, brain cancer, glioma, brain tumor, skin cancer, pancreatic cancer, breast cancer, liver cancer, bone cancer, esophageal cancer, colon cancer, gastric cancer, cervical cancer, prostate cancer, ovarian cancer, head and neck cancer, and rectal cancer, and more preferably, brain tumor, pancreatic cancer, liver cancer, lung cancer, colon cancer, and skin cancer.

Hereinafter, preferred Preparation Examples and Examples of the present disclosure will be described to assist in understanding the present disclosure. However, the following Preparation Examples and Examples are provided only to more easily understand the present disclosure, and therefore, the present disclosure is not limited thereto.

Preparation Example 1: Preparation of Mesenchymal Stem Cell Expressing Cytosine Deaminase (CD)

1.1 Isolation and Culture of Mesenchymal Stem Cell 4 ml of human bone marrow donated after the IRB examination of Ajou University Medical Center was overlaid on 4 ml of HISTOPAQUE 1077 (Sigma-Aldrich) in a sterilized 15 ml test tube, and centrifuged at 400×g for 30 minutes at room temperature using a centrifuge. After centrifugation, 0.5 ml of the intermediate buffy coat was carefully collected using a Pasteur pipette, and transferred to a test tube containing 10 ml of sterilized phosphate buffer solution (pH 7.4) After centrifugation at 250×g for 10 minutes, the supernatant was discarded, and 10 ml of phosphate buffer solution was added and gently suspended, followed by centrifugation at 250×g for 10 minutes. This procedure was repeated twice, and the final precipitate was added to a DMEM medium (Gibco) supplemented with 10% FBS (Hyclone) and dispensed in a 100 mm animal cell culture dish to obtain $1\times10^9$ cells. The culture container was placed in an incubator and cultured at 37° C. for 4 hours while supplying 5% carbon dioxide and 95% air. Subsequently, in order to remove cells that did not stick to the bottom of the culture container, the supernatant was removed. A fresh medium was added thereto, and cultured in an incubator.

The isolated mesenchymal stem cells were maintained in a $CO_2$ incubator at 37° C., and cultured in a mesenchymal stem cell culture medium [(10% FBS (Gibco)+10 ng/ml bFGF (Sigma-Aldrich)+1% penicillin/streptomycin (Gibco)+89% DMEM (Gibco)]. The cells were cultured while replacing the medium every two days. When the cells reached about 80% in the culture container, the cells were isolated using 0.25% trypsin/0.1 mM EDTA (Gibco), diluted so as to satisfy about 800 to 1,1000 cells/cm2, or 1:10 to 1:20 with the medium, and subcultured in a new culture container. Some of the cells were stored frozen by a freezing medium supplemented with 2-10% DMSO (Sigma-Aldrich, 2, 5, 10%).

1.2 Preparation of Retrovirus Including Cytosine Deaminase (CD)

A retrovirus expressing cytosine deaminase (CD), a suicide gene, was constructed. Detailed description thereof is as follows:

DNA was isolated from *E. coli* K-12 MG1655 (Korea Research Institute of Bioscience and Biotechnology), and then PCR was performed under conditions of 5 minutes at 94° C., 30 seconds at 94° C., 40 seconds at 60° C., 1 minute at 72° C., 27 cycles; 7 minutes at 72° C. using primers CD-F (5'-GAA TTC AGG CTA GCA ATG TCT CGA ATA ACG CTT TAC AAA C-3') (SEQ ID NO: 1) and CD-R (5'-GGATTC TCT AGC TGG CAG ACA GCC GC-3') (SEQ ID NO: 2). The PCR product was using a pGEM-T Easy vector cloning kit (Promega), and then a PGEM-CD vector containing the CD gene was constructed through blue-white colony screening using X-gal (5-bromo-4-chloro-3-indolyl-β-D-galactopyranoside, Sigma-Aldrich) and IPTG (Isopropyl β-D-1-thiogalactopyranoside, Sigma-Aldrich). It was confirmed that the base sequence of the obtained CD gene was identical to that of gi: 298594 of GeneBank through sequence analysis. The prepared pGEM-CD plasmid and pcDNA3.1 (Clontech) were digested with EcoRI and NotI restriction enzymes, respectively, and the CD gene isolated from the plasmid pGEM-CD and the cut plasmid pcDNA3.1 were ligated with T4 DNA ligase. Then, the obtained product was used to transform *E. coli* DH5α, a competent cell, and cultured on an LB plate containing 50 μg/ml of ampicillin and selected to obtain a plasmid pcDNA3.1-CD. This plasmid was digested with BamH I restriction enzyme and introduced into a retroviral vector capable of producing retrovirus. The obtained plasmid was isolated by a CsCl-ultra high-speed centrifuge, and transfected into FLYRD18 cell, which is a retrovirus packaging cell line, by calcium phosphate precipitation (Jordan, Nucleic Acid Research, 24, 596-601 (1996)). Then, the cells were cultured at 37° C. in an incubator while supplying 5% carbon dioxide and 95% air. After 48 hours, only the culture solution was obtained and filtered through a 0.45 μm filter membrane to obtain a retrovirus solution. The retrovirus solution was dispensed and used while storing at −70° C.

1.3 Preparation of Mesenchymal Stem Cell into which CD Gene is Introduced

The CD gene was introduced into the mesenchymal stem cell isolated and cultured in the description of 1.1, using the CD-containing retrovirus prepared in the description of 1.2. More specifically, the mesenchymal stem cell was cultured to reach about 70% in a 100 mm culture dish. Then, 3 ml of the retrovirus solution, 3 ml of the fresh mesenchymal stem cell culture medium, and 4 μg/ml of polybrene (Sigma-Aldrich) were added and cultured for 8 hours. Then, the virus solution was removed, 10 ml of mesenchymal stem cell culture medium was added and cultured for 16 hours, and then infected again with retrovirus. After this procedure was performed 1 to 3 times, the mesenchymal stem cell was finally taken off with trypsin and subcultured by 1:20 dilution with the medium. In the subculture, puromycin (Sigma-Aldrich) was added to the medium to a concentration of 2 μg/ml. The cells were screened for 2 weeks so that only cells infected with retrovirus could survive. Finally, the mesenchymal stem cell line (hereinafter, referred to as MSC/CD) continuously expressing CD, which is a suicide gene, was constructed.

Example 1. Suicide Effect and Bystander Effect of MSC/CD 1.1 Confirmation of Suicide Effect The cytosine deaminase (CD) is a suicide gene. The MSC/CD, which is a mesenchymal stem cell expressing the cytosine deaminase (CD), may convert 5-fluorocytosine (5-FC) which is a prodrug into 5-fluorouracil (5-FU) and may have a suicide effect (the cells kill themselves) and a bystander effect (peripheral cells are killed) as shown in FIG. 1. Therefore, the suicide effect and the bystander effect of the MSC/CD prepared in the description of 1.3 were confirmed. First, 10,000 MSC/CD or mesenchymal stem cells (MSCs) were cultured in a 12-well plate. From the next day, the cells were treated with the prodrug 5-FC at a concentration of 0 to 1,000 μM, and replaced with a new medium containing the drug once every two days. The medium was changed to a cell culture medium containing 0.5 mg/ml of MTT (3-(4,5-dimethyl-thiazol-2-yl)-2,5-diphenyltetrazolium bromide, Sigma-Aldrich) capable of measuring living cells on the $6^{th}$ day after treatment with 5-FC, and reacted for 2 hours at 37° C. Then, the MTT solution was removed. 500 μl of DMSO was added to each well to perform a color reaction. Then, the lysates were transferred to a 96-well plate and absorbance was measured at 540 nm using an ELISA reader (E-max, Molecular device). A schematic diagram of the experimental method and the results thereof are shown in FIG. 2, in graphs (A) and (B) thereof.

Figure 2:
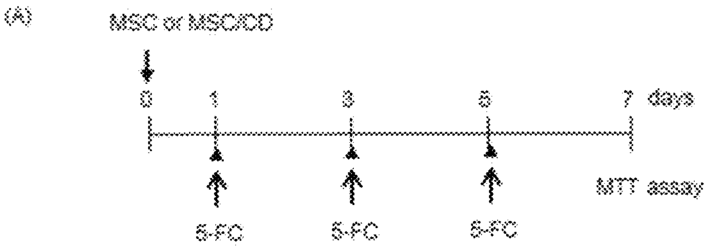
FIG. 2 shows treatment process of MSC or MSC/CD with 5-FC in graph (A) and results of the suicide effect in graph (B) derived therefrom.
Figure 2:
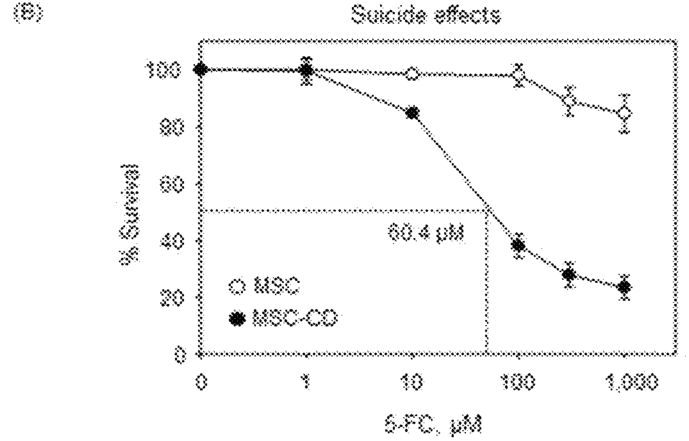

As shown in FIG. 2, in graphs (A) and (B) thereof, it was confirmed that the MSC/CD had a suicidal effect in which the living cells were reduced as the concentration of the prodrug 5-FC was increased, and $IC_{50}$ inducing 50% cell death was 60.4 μM. In the case of mesenchymal stem cell, which is the control group, it was confirmed that even if the concentration of 5-FC was increased, the cells did not kill themselves, and thus, the cytotoxic effect was not observed.

1.2 Bystander Effect 10,000 GFP-expressing U87MG (Korean Cell Line Bank KCLBNo. 30014) glioma cells and 10,000 MSC/CD or mesenchymal stem cells (MSCs) were cultured on a 12-well plate. From the next day, the cells were treated with the prodrug 5-FC at a concentration of 0 to 1,000 μM, and replaced with a new medium containing the drug once every two days, and after 6 days, the cells were obtained. Such an experimental method is briefly shown in FIG. 3, in graph (A) thereof.

Then, fluorescence images of U87MG expressing GFP remaining in the whole well were taken using a dissecting fluorescence microscope (Olympus). After the fluorescence images were taken, 200 μl of 1× passive lysis buffer (Promega) was added, and the cell lysate was placed on ice for 10 minutes and transferred to an E-tube and centrifuged at 12,000 rpm for 5 minutes, and the supernatant was transferred to a new container. 100 μl of the supernatant was transferred to a black 96-well plate, and the degree of fluorescence was measured under conditions of excitation 488 nm and emission 530 nm using a fluorimeter (GEMINI EM, molecular device). The results are shown in FIG. 3, in fluorescence images (B) and bystander effects graph (C) thereof.

Figure 3:
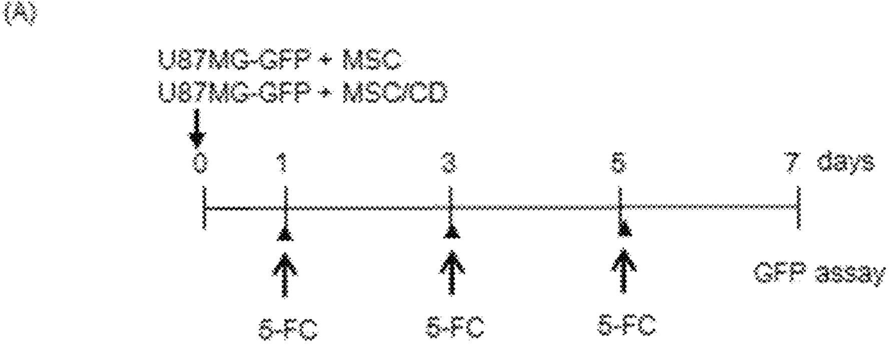
FIG. 3 shows treatment of MSC or MSC/CD with 5-FC in graph (A) and results of the bystander effect in fluorescent images (B) and (C) derived therefrom.
Figure 3:
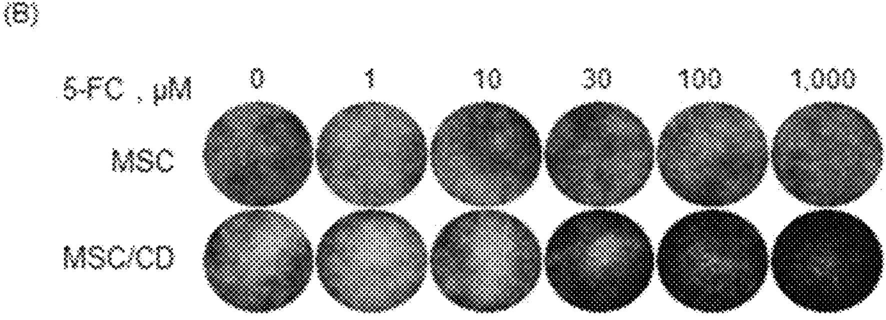
Figure 3:
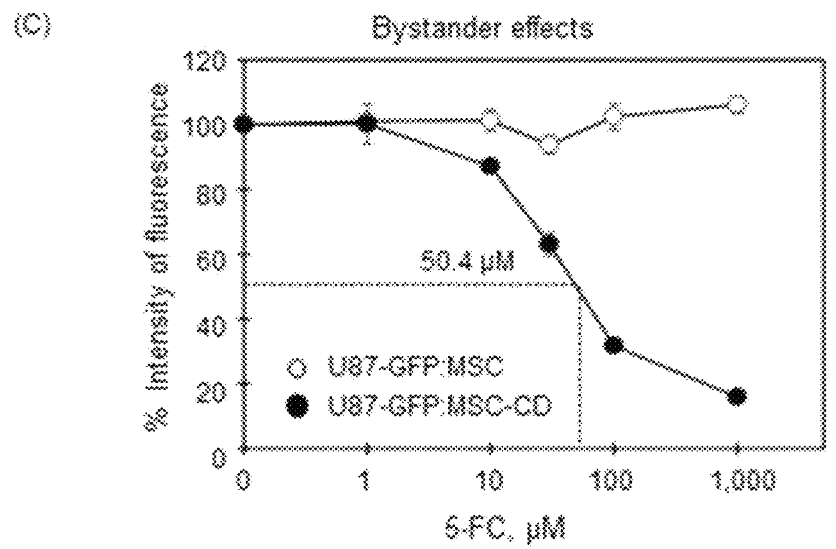

As shown in FIG. 3, in fluorescence images (B) and bystander effects graph (C) thereof, U87MG cultured with MSC/CD showed a decrease in the number of cells expressing fluorescence and a remarkable decrease in fluorescence intensity as the concentration of 5-FC was increased, but U87MG cultured with the mesenchymal stem cells in which the CD was not expressed did not show a significant difference in the number of cells expressing fluorescence and fluorescence intensity according to the concentration of 5-FC. Herein, $IC_{50}$ inducing 50% cell death was 50.48 μM. The results indicated that the MSC/CD, which is the mesenchymal stem cell into which the CD was introduced, showed not only the suicide effect but also the bystander effect in which the peripheral cells were killed together.

Preparation Example 2. Preparation of "I Cell" and "F Cell"

In the case of a cell therapy agent, the effect may vary depending on the change in the cell state under various conditions. Therefore, in order to confirm whether the cell ability was changed according to the state of MSC/CD, cells in a thawed state immediately after freezing (hereinafter, referred to as F cells (frozen cells)), and cells in a harvested state immediately from the cells during the culturing (hereinafter, referred to as I cells (immediately harvested cells)) were prepared.

In order to prepare the F cells and the I cells, respectively, the MSC/CD was cultured, and then $2\times10^6$ cells were dispensed in 1 ml of freezing medium containing 2 to 10% (2, 5, 10%) DMSO or $2\times10^6$ cells were dispensed in 1 ml of Cryostor CS10 (BioLife Solutions). The cells were frozen and stored in a liquid nitrogen container. First, in order to obtain "I cells" of MSC/CD, cells of passage 5 were dissolved at 37° C., and placed in 9 ml of culture medium. Then, the cells were centrifuged at 500 g for 5 minutes to remove the supernatant, and the precipitated cells were suspended in the culture solution, and dispensed in a 150 mm culture container. The next day, $1.5\times10^5$ cells were transferred to the 150 mm culture container, and replaced with new medium once every two days. After 6 days, the cells were collected to prepare "I cells" corresponding to passage 6.

In order to obtain the "F cells", the MSC/CD frozen and stored in the passage 6 at −130° C. or below was dissolved at 37° C. and suspended in a Plasma Solution A (CJ HealthCare Corp.) containing 9 ml of human serum albumin, followed by centrifugation at 500×g for 5 minutes, or suspended in physiological saline containing a final 7.5% dextran-40 (Daihan Pharm Co., Ltd.) and 5% human serum albumin (Green Cross Corp.), followed by centrifugation at 800×g for 10 minutes. Then, the supernatant was removed, and the precipitated cells were suspended in the culture medium and used. In other words, the F cells are cells that were not subjected to the culturing step after freezing and thawing. The I cells and the F cells were washed twice, respectively, before transplantation into the brain.

Example 1. Bystander Effect and Colony Formation of F Cells 1.1 Bystander Effect of F Cells Experiments were performed to determine whether the F cells could normally exhibit the bystander effect of MSC/CD and whether the bystander effect appeared effectively regardless of the preparation method such as the type of medium. 10,000 I cells prepared by the method of Preparation Example 2, 10,000 F cells prepared with 10% DMSO freezing medium (DMSO), and 10,000 F cells prepared with Cryostor CS10 (CS10) were washed with a Plasma Solution A, and were co-cultured in 12-well plates together with glioma U87/GFP cells in which GFP gene was transduced into U87MG (KCLB No. 30014) donated from Korean Cell Line Bank so as to express fluorescence. From the next day, the cells were treated with the prodrug 5-FC at a concentration of 0 to 1,000 μM, and replaced with a new medium containing the drug once every two days, and after 6 days, the cells were obtained. 200 μl of 1× passive lysis buffer (Promega) was added, and the cells were placed on ice for 10 minutes. The cell lysate was transferred to an E-tube and centrifuged at 12,000 rpm for 5 minutes, and the supernatant was transferred to a new container. 100 μl of the supernatant was transferred to a black 96-well plate in which light is blocked, and the degree of fluorescence was measured under conditions of excitation 488 nm and emission 530 nm using a fluorimeter (GEMINI EM, molecular device). A schematic diagram of the experimental method and the bystander effect are shown in FIG. 4, in graphs (A) and (B) thereof.

Figure 4:
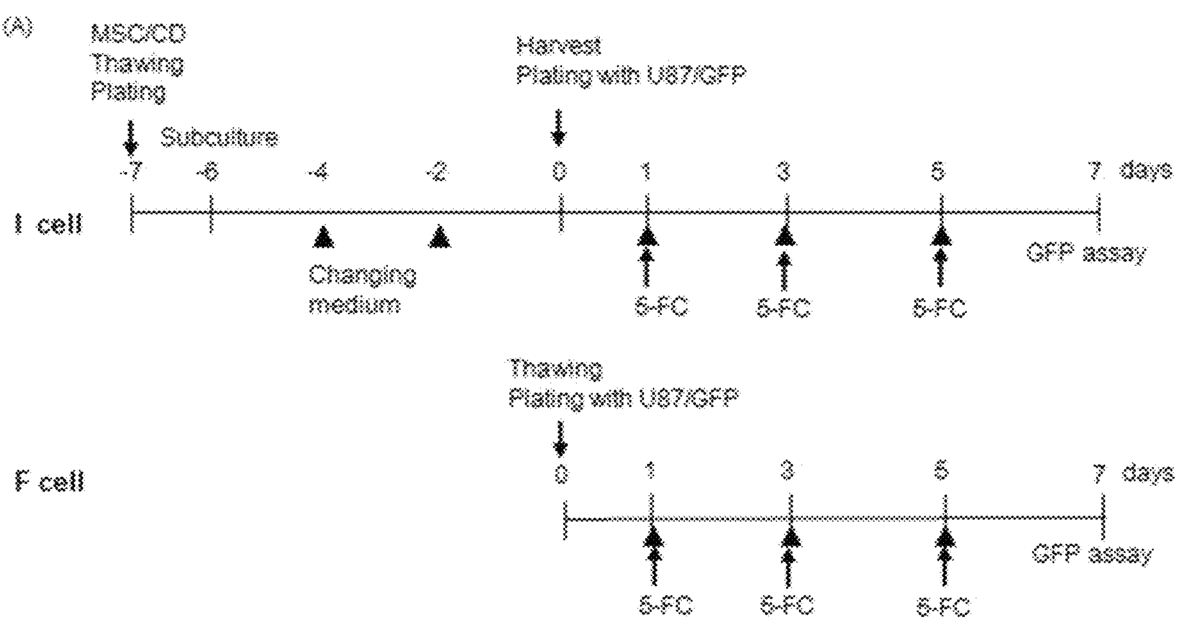
FIG. 4 shows process of cell preparation and treatment of I cell, F cell (DMSO), and F cell (CS10) in graph (A) for comparing bystander effect on respective cells and bystander effects in graph (B) on respective cells.
Figure 4:
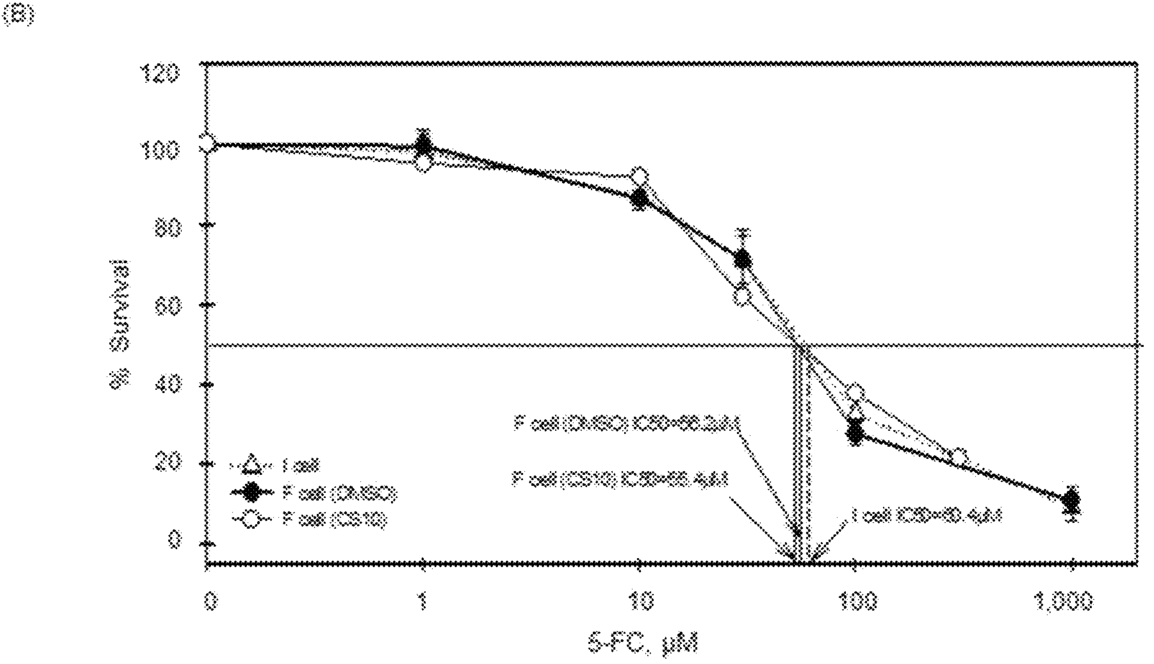

As shown in FIG. 4, in graphs (A) and (B), the $IC_{50}$ values indicating concentration at which 50% of apoptosis is caused, was 60.4 μM for I cells, 56.2 μM for F cells prepared with 10% DMSO freezing medium (DMSO), and 55.4 μM for F cells prepared with Cryostor CS10 (CS10). These results indicated that the F cell was a cell that could effectively exhibit the bystander effect as compared to the I cell, and thus it was confirmed that the F cell exhibited the bystander effect more excellently as compared to the I cell regardless of the preparation method using the DMSO medium or the CS10 medium.

Therefore, hereinafter, the F cells prepared with the 10% DMSO freezing medium were used among the F cells prepared in Preparation Example 2.

1.2. Colony Forming Effect of F Cells

A colony forming unit assay was performed to confirm whether the F cells prepared by freezing and thawing as in Preparation Example 2 exhibited a difference in proliferative capacity as compared to the I cells. The I cells prepared as in Preparation Example 2 and corresponding the same passage and the F cells prepared with 10% DMSO freezing medium were counted with Countess (Invitrogen), and then 100 cells were placed in a 100 mm culture container, respectively, and cultured while replacing the medium with a new medium once every two days. After 2 weeks, the cells were fixed with 10% formalin for 10 minutes, washed with phosphate buffer solution (Gibco), stained with a crystal violet solution (Sigma-Aldrich) for 10 minutes, and washed three times with water to obtain images by Versa doc (BioRad). The number of colonies formed by growing one cell for 2 weeks was visually counted, and shown in FIG. 5, in image (A) and graph (B) thereof.

Figure 5:
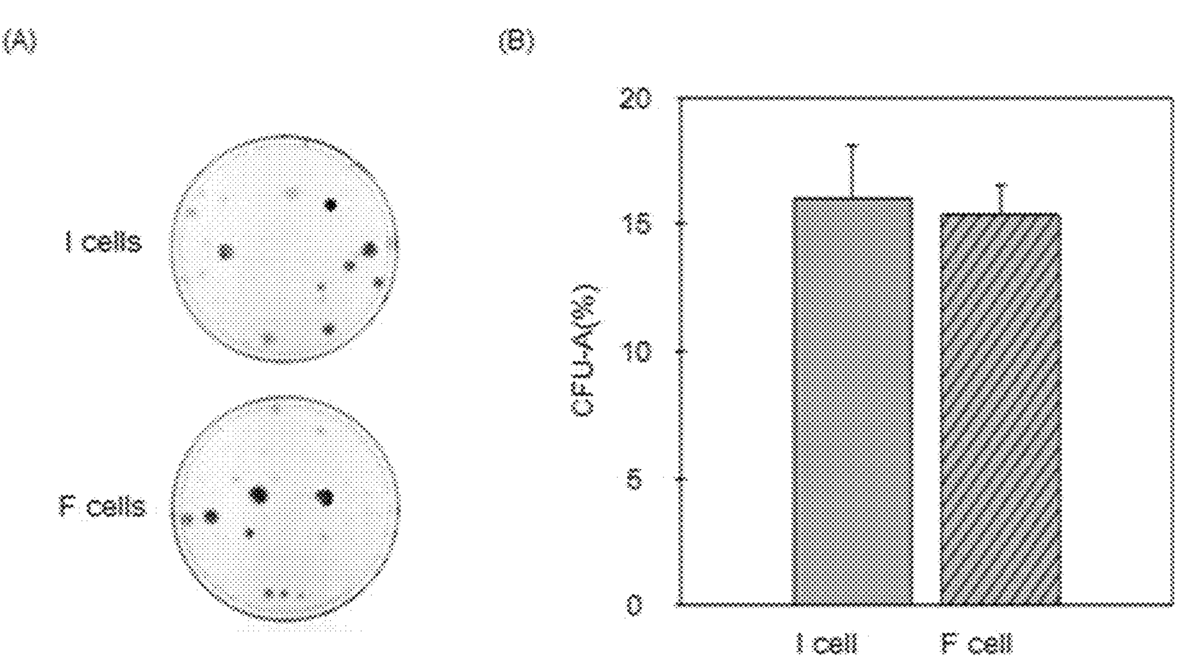
FIG. 5 shows a microscopic observation of a colony forming ability of the I cell and the F cell in images (A), and a graph for comparing quantitative analysis results using CFU-A (colony forming unit assay) in graph (B).

As shown in FIG. 5, in image (A) and graph (B) thereof, it was confirmed that the I and F cells had no difference in the colony forming ability. These results indicated that the increased bystander effect of the F cells as compared to that of the I cells was not caused by an increase in the number of cells such as an increase in colony formation, and that the F cells themselves exhibited more excellent bystander effect as compared to that of the I cells.

Example 2. Anti-Cancer Effect of F Cell 2.1. Anti-Cancer Effect of F Cell on Brain Tumor In order to confirm the anti-cancer effect of the F cells on brain tumor, an orthotopic glioma model was constructed. First, 7-week-old immunodeficient nude mice (central experimental animals) were anesthetized and their mouths and ears were fixed in a stereotaxic frame. The head to be incised was sterilized with 70% ethanol, and the crown of head was vertically incised to about 0.5 cm. $3\times10^5$/3 μl of U87MG glioma cells expressing LacZ were transplanted at a rate of 0.3 μl/min at the brain coordinates of AP=+0.5 mm, ML=−1.8 mm, and DV=−3 mm, thereby constructing a brain tumor orthotopic glioma model. On the 3rd day after transplantation of U87MG glioma cells expressing LacZ, the F cells prepared in Preparation Example 2 were suspended in a Plasma Solution A, followed by centrifugation at 500×g for 5 minutes. The supernatant was discarded, and the washing procedure was repeated once or twice. Then, the cell suspension was prepared to have a concentration of $3\times10^5$/6 μl. The cell suspension was transplanted at a rate of 0.3 μl/min at the brain coordinates of AP=+0.5 mm, ML==1.8 mm, and DV=−3 mm. From the next day after the cell transplantation, 5-FC (15 mg/ml physiological saline) was intraperitoneally injected at a dose of 500 mg/kg for one week. To compare the anti-cancer effect of the F cells, the I cells prepared in Preparation Example 2 were transplanted in the same manner, and 5-FC (15 mg/ml physiological saline) was intraperitoneally injected at a dose of 500 mg/kg for one week from the next day after the cell transplantation.

On the 28th day after glioma cell transplantation, the animals were anesthetized, and perfused with physiological saline by inserting an injection needle into the left ventricle of the animals, and then, perfused with 10% formalin solution. The brain was extracted and fixed on a mouse brain matrix (Stoelting). Then, the brain was cut horizontally at intervals of 1 mm, and put in the same fixing fluid for 30 minutes, thereby fixing the brain slice. The brain slice was washed three times with phosphate buffered saline, immersed in phosphate buffered saline containing 20 mg/ml of X-gal (5-bromo-4-chloro-3-indolyl-β-D-galactopyranoside, Koma Biotech), 5 mM potassium ferrocyanide/ferricyanide (Sigma-Aldrich), 2 mM $MgCl_2$, and 0.02% NP40, and reacted at 37° C. for 16 hours. An image of the brain tumor was obtained through an anatomic microscope. A size of the tumor was calculated using the image j (NIH) program and the following Equation, and the results are shown in FIG. 6, in graph (A), images (B), and graph (C) thereof.

$$\text{Tumor volume}\,(\text{mm}^3) = \sum \frac{\text{Number of pixels of tumor area}}{\text{Number of pixels per unit area}} \times 0.5\text{ mm}$$

Figure 6:
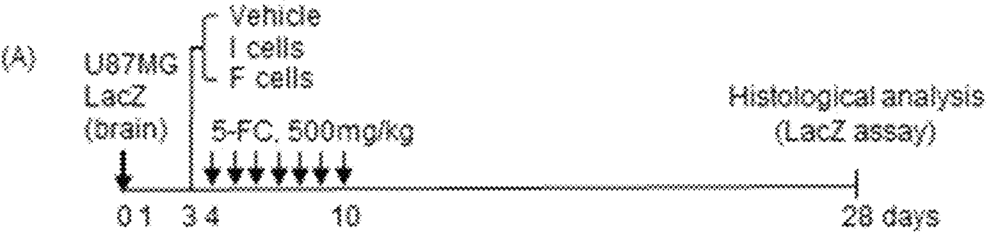
FIG. 6 shows a process of treating the I-cell or the F-cell with 5-FC in a brain tumor model in graph (A), results of brain tumor changes following the treatment observed under a dissecting microscope obtained by observing brain tumor changes by the treatment in images (B), and tumor volume changes in graph (C).
Figure 6:
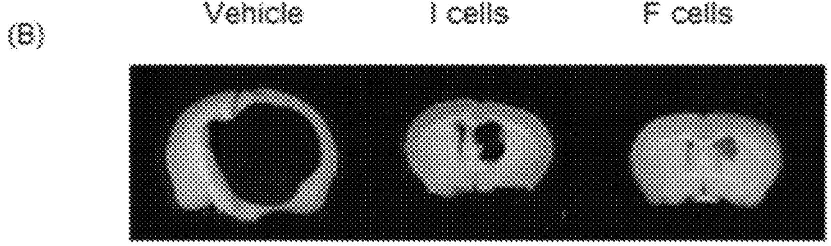
Figure 6:
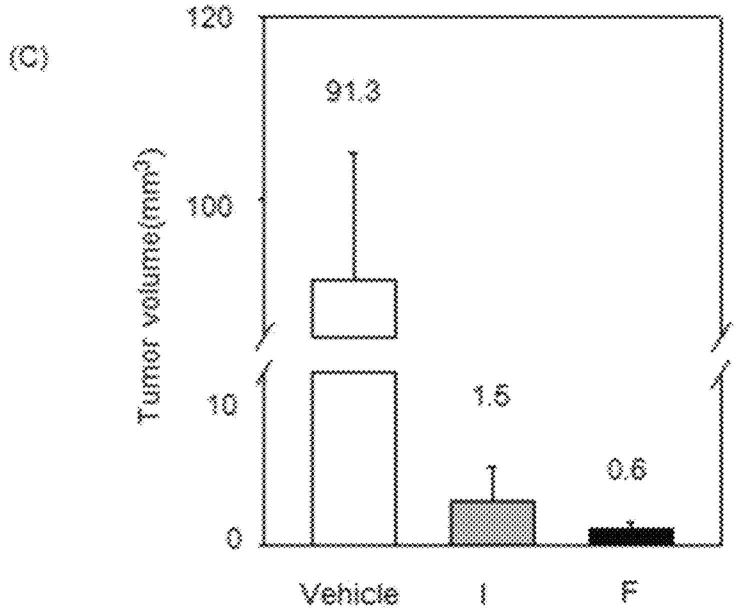

As shown in FIG. 6, in images (B) thereof, in the F cell transplantation group, the volume of the brain tumor was remarkably decreased, and more excellent effect was exhibited as compared to the I cell. The computed mean size of the tumor was 91.3 mm$^3$ in the vehicle control group, 1.5 mm$^3$ in the I cell transplantation comparison group, but 0.6 mm$^3$ in the F cell transplantation animal group. That is, according to the in vivo results, it was confirmed that the F cell had a tumor-reducing effect twice more than that of the I cell among the MSC/CD, and the F cell could be a more effective anti-cancer agent.

2.2. Anti-Cancer Effect of F Cell on Liver Cancer $1\times10^5$ Huh7 liver cancer cells (KCLB No. 60104) were suspended in 100 μl of a phosphate buffer solution containing 20% Matrigel (BD), and transplanted subcutaneously in 7-week-old immunodeficient nude mice (Balb/c nude). After 14 days from transplantation, when the tumor size reached 10 to 100 mm$^3$, the I cells and the F cells prepared in Preparation Example 2 were injected. More specifically, the I cells and F cells prepared in Preparation Example 2 were suspended in the phosphate buffer solution, followed by centrifugation at 500×g for 5 minutes. This procedure was repeated twice, and then the I cells or the F cells were prepared to have concentration of $1\times10^6$/100 μl in the phosphate buffer solution and injected directly into the tumor using a syringe. From the next day after the I cell and F cell injection, 5-FC (15 mg/ml physiological saline) was intraperitoneally injected at a dose of 500 mg/kg for one week. The size of the tumor was measured once or twice weekly using a digital caliper, and the tumor volume was calculated using the following Equation, and the results are shown in FIG. 7, in graph (A) and animal images (B) thereof.

$$\text{Subcutaneous tumor volume}\,(\text{mm}^3) = \text{Width (mm)} \times \text{Length (mm)} \times \text{Height (mm)} \div 6$$

[For Measurement of Tumor Volume, see Cancer Chemother. Pharmacol. (1989) 24:148-154]

Figure 7:
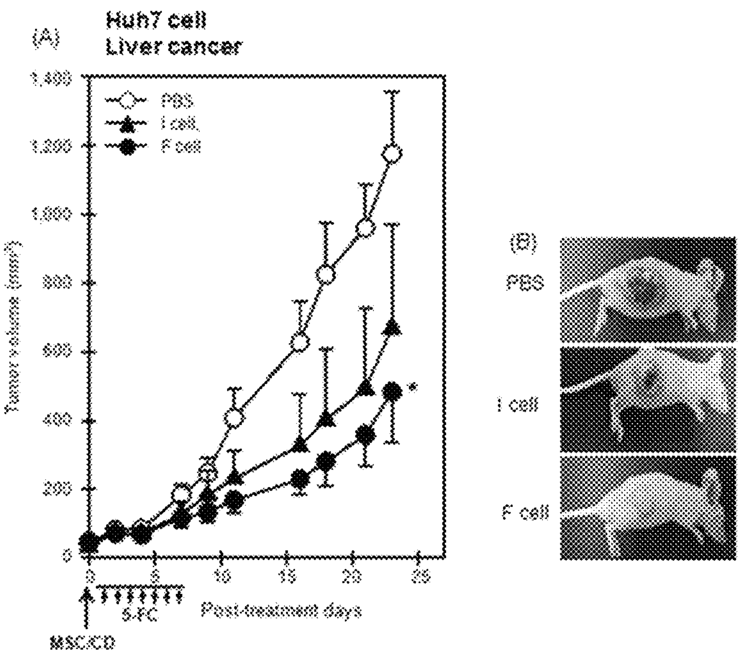
FIG. 7 shows a graph for tumor volume changes according to the I cell or F cell treatment in graph (A) in subcutaneous tumor models in which liver cancer cells are implanted subcutaneously, and representative tumor models showing an external size of the tumor in images (B).

As shown in graph (A) of FIG. 7, the tumor volume was more effectively decreased in the experimental group treated with the F cell, confirming that the F cell had more excellent anti-cancer effect than the I cell. As shown in animal images (B) of FIG. 7, the increased anti-cancer effect was visually confirmed in the subcutaneous tumor model transplanted with the liver cancer cells, and thus, it was confirmed that the therapeutic effect of F cells was excellent (*, $p<0.05$ upon comparison with the PBS group).

2.3. Anti-Cancer Effect of F Cell on Pancreatic Cancer

BxPC3 pancreatic cancer cells (ATCC No. CRL-1687™) had a rapid growth rate and severe ulceration, and thus, $1\times10^6$ BxPC3 pancreatic cancer cells, the I cells, and the F cells were injected simultaneously. More specifically, the I cells and F cells prepared in Preparation Example 2 were suspended in the phosphate buffer solution, followed by centrifugation at 500×g for 5 minutes. This procedure was repeated twice, and then the I cells or the F cells were prepared to have concentration of $1\times10^6$/100 μl in the phosphate buffer solution. $1\times10^6$ I cells or F cells were suspended in 100 μl of a phosphate buffer solution containing 20% Matrigel (BD), and simultaneously transplanted subcutaneously in 7-week-old immunodeficient nude mice (Balb/c nude). From the next day after the cell injection, 5-FC (15 mg/ml physiological saline) was intraperitoneally injected at a dose of 500 mg/kg for one week.

Figure 8:
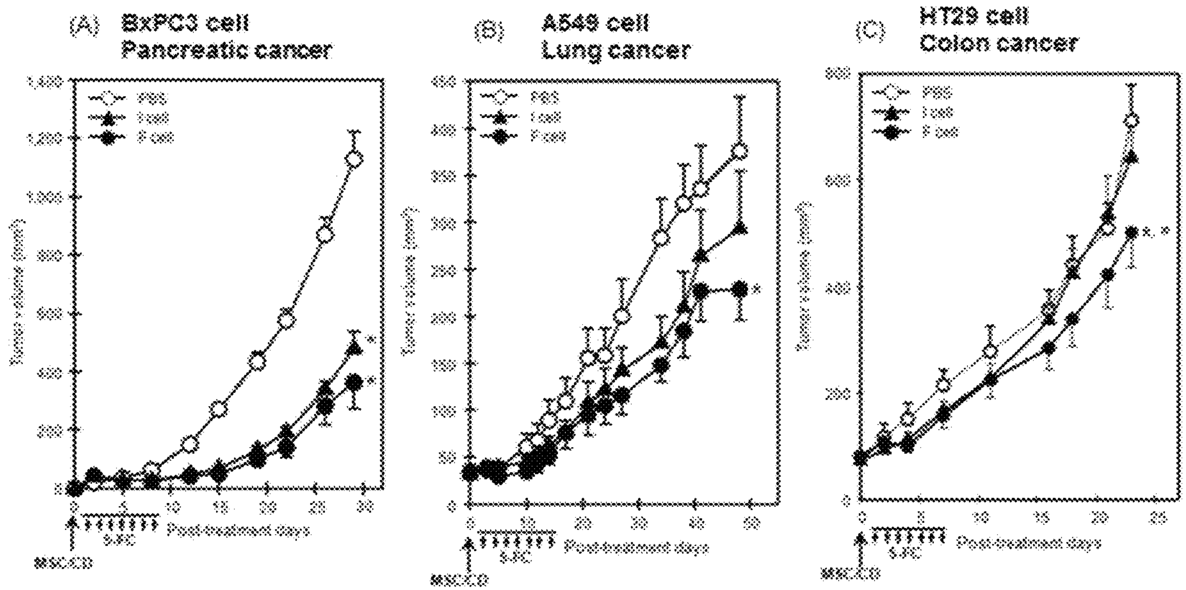
FIG. 8 shows tumor volume changes according to the I cell or F cell treatment, in subcutaneous tumor models in which pancreatic cancer cells are implanted subcutaneously in graph (A), in subcutaneous tumor models in which lung cancer cells are implanted subcutaneously in graph (B), and in subcutaneous tumor models in which colon cancer cells are implanted subcutaneously in graph (C).

The tumor volume was measured in the same manner as in Example 2.2, and the measured tumor volume change was shown in FIG. 8, in graph (A) thereof.

As shown in graph (A) of FIG. 8, the tumor volume was more effectively decreased in the experimental group treated with the F cell, confirming that the F cell had more excellent anti-cancer effect than the I cell, and had excellent therapeutic effect in the pancreatic cancer subcutaneous tumor model (*, $p<0.05$ upon comparison with the PBS group).

2.4. Anti-Cancer Effect of F Cell on Lung Cancer $5\times10^6$ A549 lung cancer cells (ATCC No. CCL-185™) were suspended in 100 μl of a phosphate buffer solution containing 20% Matrigel (BD), and transplanted subcutaneously in 7-week-old immunodeficient nude mice (Balb/c nude). After 8 days from transplantation, when the tumor size reached 20 to 50 $mm^3$, the I cells and the F cells prepared in Preparation Example 2 were injected. More specifically, the I cells and F cells prepared in Preparation Example 2 were suspended in the phosphate buffer solution, followed by centrifugation at 500×g for 5 minutes.

This procedure was repeated twice, and then the I cells or the F cells were prepared to have concentration of $1\times10^6$/100 μl in the phosphate buffer solution and injected directly into the tumor using a syringe. From the next day after the I cell and F cell injection, 5-FC (15 mg/ml physiological saline) was intraperitoneally injected at a dose of 500 mg/kg for one week. The tumor volume was measured in the same manner as in Example 2.2, and the measured tumor volume change was shown in FIG. 8, in graph (B) thereof.

As shown in graph (B) of FIG. 8, the tumor volume was more effectively decreased in the experimental group treated with the F cell, confirming that the F cell had more excellent anti-cancer effect than the I cell, and had excellent therapeutic effect in the lung cancer subcutaneous tumor model (*, $p<0.05$ upon comparison with the PBS group).

2.5. Anti-Cancer Effect of F Cell on Colon Cancer $5\times10^6$ HT29 colon cancer cells (ATCC No. HTB-38™) were suspended in 100 μl of a phosphate buffer solution containing 20% Matrigel (BD), and transplanted subcutaneously in 7-week-old immunodeficient nude mice (Balb/c nude). After the transplantation, when the tumor size reached 40 to 100 $mm^3$, the I cells and the F cells prepared in Preparation Example 2 were injected. More specifically, the I cells and F cells prepared in Preparation Example 2 were suspended in the phosphate buffer solution, followed by centrifugation at 500×g for 5 minutes.

This procedure was repeated twice, and then the I cells or the F cells were prepared to have concentration of $1\times10^6$/100 μl in the phosphate buffer solution and injected directly into the tumor using a syringe. From the next day after the I cell and F cell injection, 5-FC (15 mg/ml physiological saline) was intraperitoneally injected at a dose of 500 mg/kg for one week. The tumor volume was measured in the same manner as in Example 2.2, and the measured tumor volume change was shown in FIG. 8, in graph (C) thereof.

As shown in graph (C) of FIG. 8, the tumor volume was more effectively decreased in the experimental group treated with the F cell, confirming that the F cell had more excellent anti-cancer effect than the I cell, and had excellent therapeutic effect in the colon cancer subcutaneous tumor model (*, $p<0.05$ upon comparison with the PBS group, and #, $p<0.05$ upon comparison with the I cell group).

From the above results, it was confirmed that the F cell had an excellent anti-cancer effect in various types of cancer such as brain tumor, liver cancer, lung cancer, colon cancer, and exhibited a more excellent anti-cancer effect in all types of cancer as compared to the I cell.

Example 3. Synergistic Effect of Combination Therapy of F Cells (In Vitro)

3.1 In Vitro Combination Therapy with Temozolomide 10,000 GFP-expressing U87MG (Korean Cell Line Bank KCLBNo. 30014) glioma cells and 10,000 F cells or mesenchymal stem cells (MSCs) were cultured in a 12-well plate. The next day, the cells were treated with temozolomide (TMZ) at a concentration of 0 to 1000 μM and the prodrug 5-FC at a concentration of 0 to 1,000 μM, and replaced with a new medium containing the drug once every two days, and after 6 days, the cells were obtained. A schematic diagram of this experiment is shown in graph (A) of FIG. 9. Fluorescence images of U87MG expressing GFP remaining in the whole well were taken using a dissecting fluorescence microscope (Olympus), and cell death was confirmed. The results are shown in the fluorescence images (D) of FIG. 9.

Figure 9:
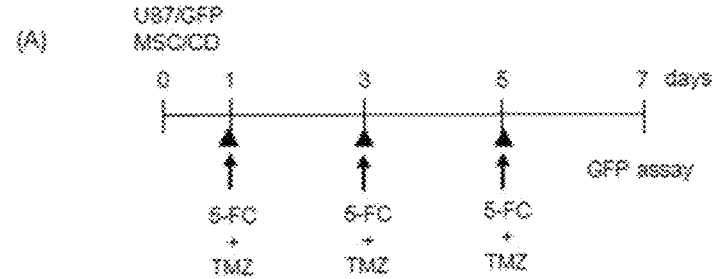
FIG. 9 shows F cells+5-FC+TMZ combination therapy in graph (A), the bystander effects derived therefrom in graphs (B) and (C), confirmation on results of cell death through fluorescence images of U87MG expressing GFP in images (D), and isobologram results of $IC_{50}$ values in graph (E).
Figure 9:
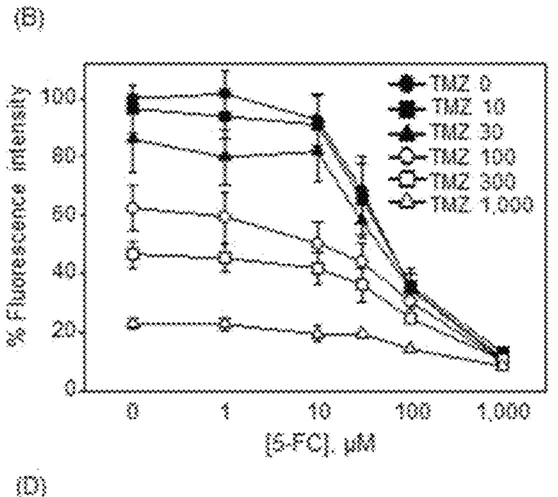
Figure 9:
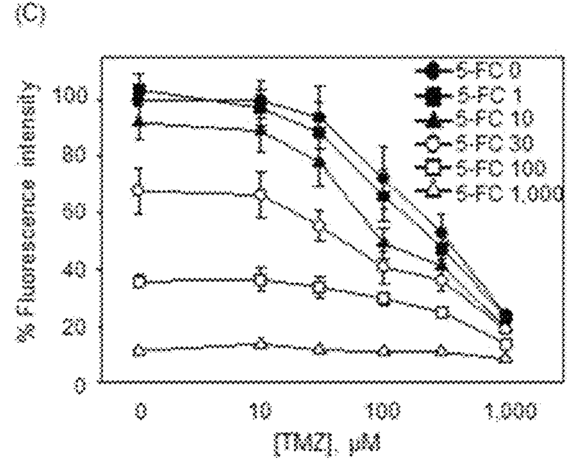
Figure 9:
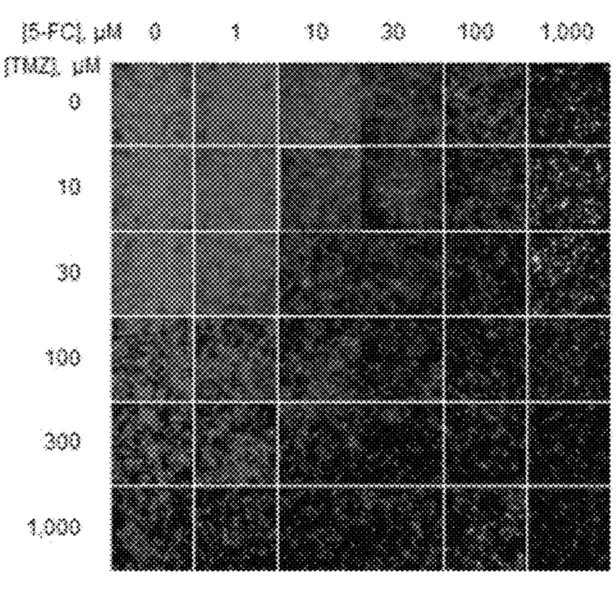
Figure 9:
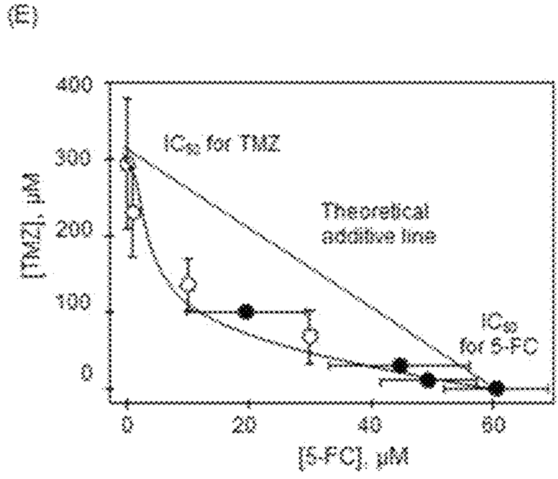

As shown in the fluorescence images (D) of FIG. 9, it was confirmed that the fluorescence expression was decreased according to an increase in the temozolomide treatment concentration and an increase in the 5-FC treatment concentration, and the bystander effect of the F cell was elevated by the combined administration with temozolomide.

After the fluorescence images were taken, 200 μl of 1× passive lysis buffer (Promega) was added, and the cells were placed on ice for 10 minutes. The cell lysate was transferred to an E-tube and centrifuged at 12,000 rpm for 5 minutes, and the supernatant was transferred to a new container. 100 μl of the supernatant was transferred to a black 96-well plate, and the intensity of fluorescence was measured under conditions of excitation 488 nm and emission 530 nm using a fluorimeter (GEMINI EM, molecular device) (graphs (B) and (C) of FIG. 9). The actual $IC_{50}$ values obtained by treating the two types of anti-cancer agents together were expressed as isobologram. The solid line connecting the $IC_{50}$ values when the anti-cancer agent was treated alone in the isobologram is a theoretical additive line, which means that when the values obtained by simultaneously treating two anti-cancer agents are on the solid line, there is simply an additive effect. On the other hand, it means that when the value is lower than the solid line, there is a synergistic effect, and conversely, when the value is above the solid line, there is an antagonistic effect. The results are shown in FIG. 9, in graph (E) thereof.

As shown in graph (E) of FIG. 9, all of the marked points when the MSC/CD was treated with 5-FC and temozolomide in combination were present at the lower side as compared to the $IC_{50}$ values when the anti-cancer agent was treated alone, which was confirmed that there was a synergistic effect which is more excellent than the additive effect obtained by simple treatment with the two anti-cancer agents together.

3.2 In Vitro Combination Therapy with Carmustine (BCNU)

10,000 GFP-expressing U87MG glioma cells, i.e., U87/GFP (Korean Cell Line Bank KCLBNo. 30014) and 10,000 F cells (MSC/CD) were cultured in a 12-well plate. From the next day, the cells were treated with Carmustine (BCNU, Sigma) at a concentration of 0 to 300 μM and the prodrug 5-FC at a concentration of 0 to 300 μM, and cultured for 6 days while replacing with a new medium containing the drug once every two days. On the $7^{th}$ day, the culture solution was removed, 200 μl of 1× passive lysis buffer (Promega) was then added to each well, and each well was allowed to stand at 4° C. for 10 minutes. The cell lysate was collected and centrifuged at 12,000 rpm for 5 minutes to obtain a supernatant. 100 μl of the supernatant was transferred to a black 96-well plate in which light is blocked, and the intensity of fluorescence was measured under conditions of excitation 488 nm and emission 530 nm using a fluorimeter (GEMINI EM, molecular device). A schematic diagram of this experiment is shown in graph (A) of FIG. 10.

Figure 10:
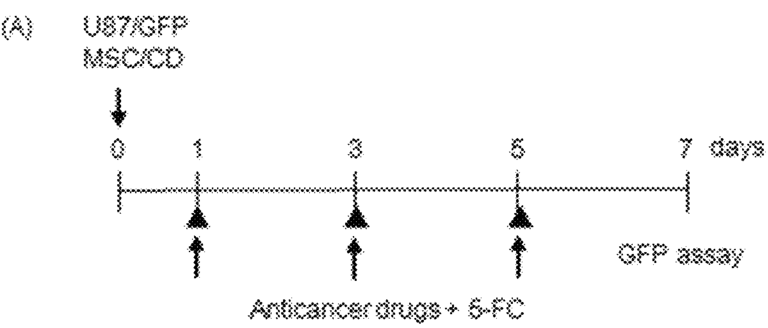
FIG. 10 shows F cells+5-FC+anti-cancer agent combination therapy in graph (A), isobologram results of $IC_{50}$ values of carmustine in graph (B), and isobologram results of $IC_{50}$ values of irinotecan in graph (C), respectively, in anti-cancer agent combination therapy.
Figure 10:
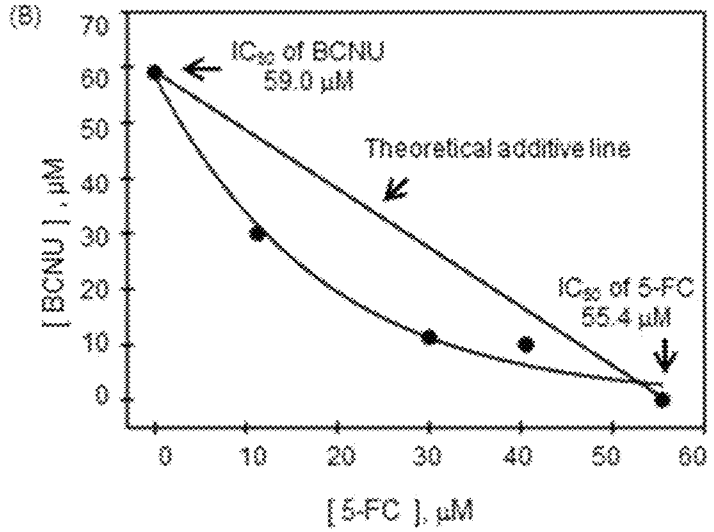
Figure 10:
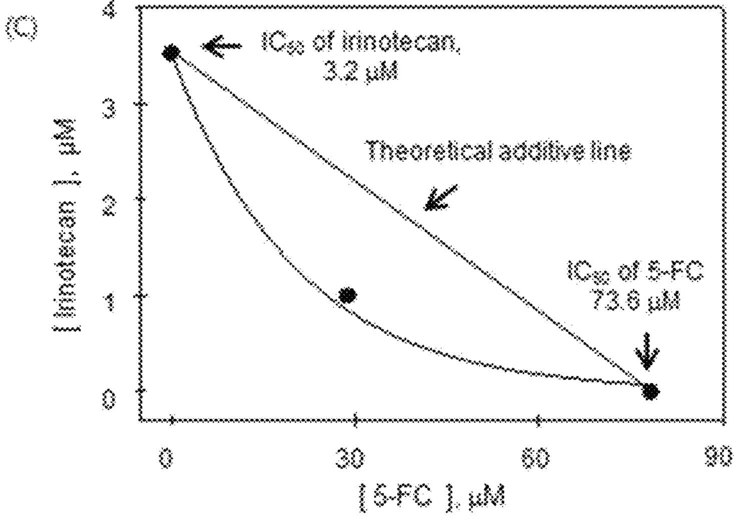

The actual $IC_{50}$ values obtained by treatment with the two types of anti-cancer agents together were expressed as isobologram, and the results were shown in FIG. 10, in graph (B) thereof.

As shown in graph (B) of FIG. 10, all of the marked points when U87/GFP was treated with [F cell (MSC/CD)+5-FC] and carmustine in combination were present at the lower side of the solid line as compared to the $IC_{50}$ values when the anti-cancer agent was treated alone, which was confirmed that there was a synergistic effect which is more excellent than the additive effect obtained by simple treatment with the two anti-cancer agents together.

3.3 In Vitro Combination Therapy with Irinotecan 10,000 U87/GFP and 10,000 F cells (MSC/CD) were cultured in a 12-well plate. From the next day, the cells were treated with Irinotecan (Sigma) at a concentration of 0 to 30 μM and the prodrug 5-FC at a concentration of 0 to 300 μM, and cultured for 6 days while replacing with a new medium containing the drug once every two days. On the 7th day, the culture solution was removed, 200 μl of 1× passive lysis buffer was then added to each well, and each well was allowed to stand at 4° C. for 10 minutes. The cell lysate was collected and centrifuged at 12,000 rpm for 5 minutes to obtain supernatant. 100 μl of the supernatant was transferred to a black 96-well plate in which light is blocked, and the intensity of fluorescence was measured under conditions of excitation 488 nm and emission 530 nm using a fluorimeter (GEMINI EM). The actual $IC_{50}$ values obtained by treatment with the two types of anti-cancer agents together were expressed as isobologram, and the results were shown in graph (C) of FIG. 10.

As shown in graph (C) of FIG. 10, the $IC_{50}$ values obtained by treatment with irinotecan alone in the isobologram was 3.2 μM and the $IC_{50}$ values obtained by treatment with 5-FC was 73.6 μM, and these $IC_{50}$ values were connected to obtain a theoretical additive line representing a simple additive effect. The $IC_{50}$ values obtained when U87/GFP was treated with [F cell (MSC/CD)+5-FC] and irinotecan in combination were present at the lower side of the solid line as compared to the $IC_{50}$ values when the anti-cancer agent was treated alone, which was confirmed that there was a synergistic effect which is more excellent than the effect obtained by simple treatment with the two anti-cancer agents together.

Since all of temozolomide, carmustine, and irinotecan are known as anti-cancer agents that act on proliferating cells, if they affect the survival of not only U87/GFP cells but also proliferating F cells, the anti-cancer effect of [F cell (MSC/CD)+5-FC] might be reduced. However, contrary to the expectation, it was confirmed from graph (E) of FIG. 9 that the synergistic effect could be obtained which was rather elevated as compared to the administration of the anti-cancer agent alone or in combination, when [F cell (MSC/CD)+5-FC] was used in combination with temozolomide. That is, the synergistic effect is an unexpected effect that is not capable of being expected in the existing combination therapies.

3.4 In Vivo Combination Therapy with Temozolomide

The synergistic effects confirmed in the above-descriptions of 3.1 to 3.3 were further confirmed and verified in vivo. On the $6^{th}$ days after transplantation of U87MG glioma cells expressing LacZ, the F cells prepared in Preparation Example 2 were suspended in a Plasma Solution A, followed by centrifugation at 500×g for 5 minutes. The supernatant was discarded, and the washing procedure was repeated twice. Then, the cell suspension was prepared to have a concentration of $3\times10^5$/6 μl. The cell suspension was transplanted at a rate of 0.3 μl/min at the brain coordinates of AP=+0.5 mm, ML=−1.8 mm, and DV=−3 mm. From the next day after the cell transplantation, 5-FC (15 mg/ml physiological saline) was intraperitoneally injected at a dose of 500 mg/kg for one week. After 4 days, temozolomide (1 mg/ml in DMSO:physiological saline=1:1) was intraperitoneally injected at a dose of 5 mg/kg for 5 days. On $28^{th}$ day, brain tissues were obtained from 8 animals in each animal group and X-gal staining was performed in the same manner as in Example 2 to measure the size of brain tumor. The experimental procedure is shown in graph (A) of FIG. 11, and the changes in measured brain tumor size are shown in images (B) and graph (C) of FIG. 11.

Figure 11:
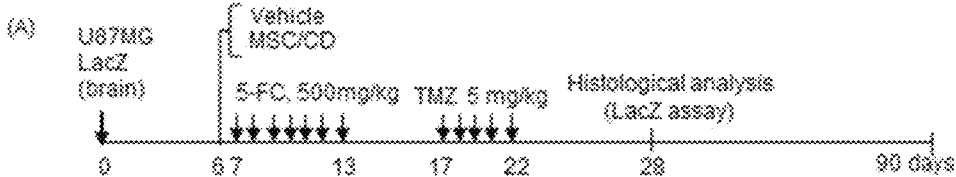
FIG. 11 shows process of F cells+5-FC+temozolomide (TMZ) combination therapy in graph (A), the results of brain tumor changes following the treatment observed under a dissecting microscope showing brain tumor changes in images (B), tumor volume changes in graph (C), and synergistic effects in improvement of survival rates in graph (D) by the combination therapy.
Figure 11:
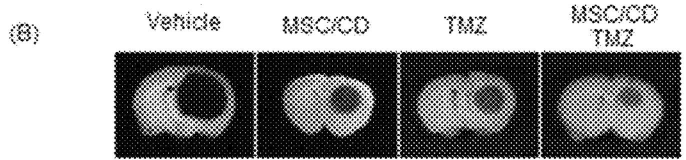
Figure 11:
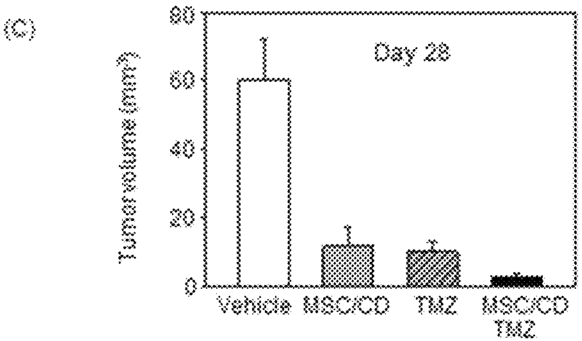
Figure 11:
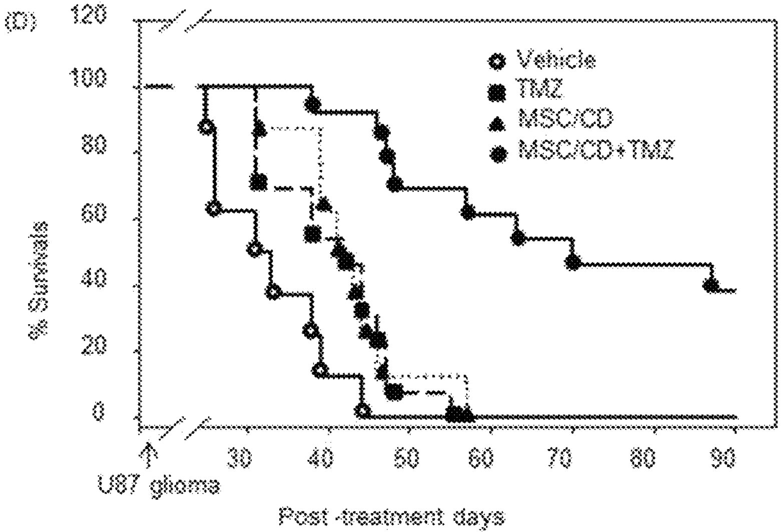

As shown in images (B) and graph (C) of FIG. 11, the average size of vehicle control tumors was 59.8 $mm^3$, whereas the average size of the animal group into which the F cells were transplanted was 11.8 $mm^3$, the average size of the animal group treated with temozolomide alone was 9.9 $mm^3$, and the average size of the animal group into which the F cells+temozolomide were transplanted was 2.7 $mm^3$. The animal group into which the F cells and temozolomide combination therapy were transplanted had the most reduced average size of the tumor, and showed the most excellent anti-cancer effect.

In addition, the survival rate according to the treatment of brain tumor was measured up to 90 days, and the results were compared in each experimental group and showed in graph (D) of FIG. 11.

As shown in graph (D) of FIG. 11, the median survival in the control group was 32 days, but prolonged to 42 days in the F cell treatment group and 42 days in the temozolomide treatment group. In particular, the median survival was prolonged to 70 days in the group with the F cell and temozolomide combination therapy, and a remarkable improvement in the survival rate was observed even in comparison with the group treated with the anti-cancer agent alone as well as the control group.

This suggests that the combination therapy with F cell showed a remarkably excellent effect even in the combination therapy with the existing anti-cancer agents, and thus, the combination therapy with F cell is able to be utilized as a remedy for improving the existing chemotherapy.

Example 4. Subcutaneous Tumor Treatment Effect of F Cells

To determine whether the F-cell could exhibit the anti-cancer effect in tumors other than brain tumor, U87MG glioma cells were transplanted into subcutaneous tissue to construct a non-brain cancer model. $1\times10^6$ U87MG glioma cells were suspended in 100 μl of a phosphate buffer solution containing 20% Matrigel (BD), and transplanted subcutaneously in 7-week-old immunodeficient nude mice. The size of the tumor was measured twice weekly using a digital caliper, and the tumor volume was calculated using the following Equation.

$$\text{Subcutaneous tumor volume } (mm^3)=\text{Width}(mm)\times\text{Length}(mm)\times\text{Height}(mm)+6$$

When the size of the tumor reached 30 $mm^3$ or more on $20^{th}$ day after the U87MG glioma cells were transplanted into the subcutaneous tissue, the I cells and F cells prepared in Preparation Example 2 were suspended in a Plasma Solution A, and centrifuged at 500× g for 5 minutes. This procedure was repeated twice, and then the I cells or the F cells were prepared to have concentration of $1\times10^6$/100 μl in the Plasma Solution A and injected directly into the tumor using a syringe. From the next day after the I cell and F cell injection, 5-FC (15 mg/ml physiological saline) was intraperitoneally injected at a dose of 500 mg/kg for one week. After one week from the administration of 5-FC was discontinued, temozolomide (Sigma-Aldrich) was intraperitoneally injected at a dose of 5 mg/kg for 5 days. Such an experimental method is briefly shown in graph (A) of FIG. 12. The measured tumor volume change is shown in graph (B) of FIG. 12. The Kaplan Meier survival graph obtained by measuring the lifespan of nude mice in the subcutaneous tumor model is shown in graph (C) of FIG. 12.

Figure 12:
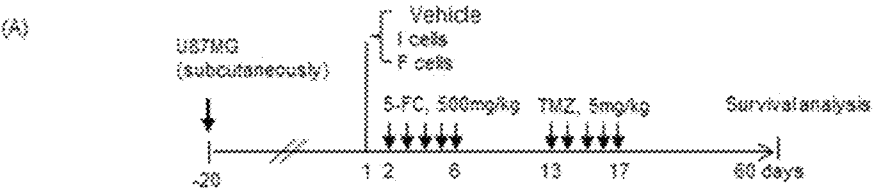
FIG. 12 shows the analysis process on effects of the I cell or the F cell+5-FC+temozolomide (TMZ) combination therapy in the subcutaneous tumor models in graph (A), tumor volume changes in graph (B), and synergistic effects of the F cell+5-FC+temozolomide (TMZ) in analysis of survival rates in graph (C).
Figure 12:
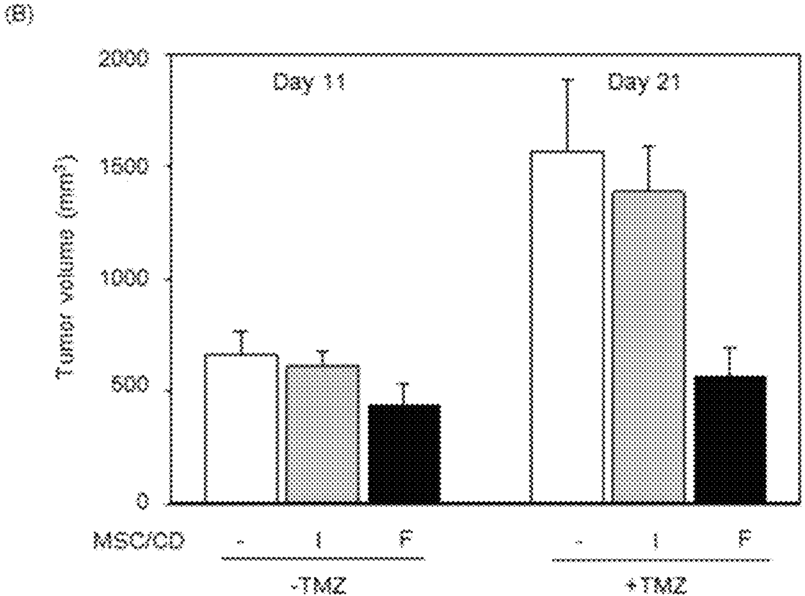
Figure 12:
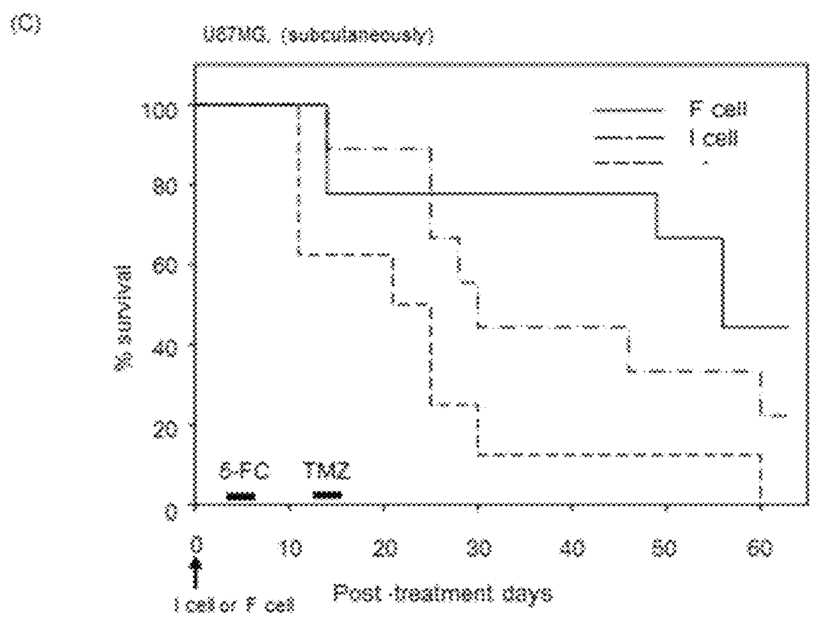

As shown in graph (B) of FIG. 12, it was confirmed that the tumor volume was more effectively decreased in the experimental group treated with F cells until the $11^{th}$ day before the administration of temozolomide, and the F cells showed more excellent anti-cancer effect than the I cells. Further, on the $21^{st}$ day after the administration of temozolomide, the tumor volume inhibitory effect in the F cell treatment group was confirmed to be very remarkable as compared to the non-treatment group (the control group) and the I cell treatment group. In addition, as shown in graph (C) of FIG. 12, the median survival of the control group was 23 days, and the median survival of the I cell treatment group was 30 days, whereas the F cell treatment group showed the median survival of 58 days, and thus, the life extension effect was also the greatest in the animal group treated with the F cells. Therefore, it may be appreciated that the F cells have excellent therapeutic effect in the subcutaneous tumor model, and in particular, exhibit a synergistic therapeutic effect through combination therapy with temozolomide, which demonstrates superiority of the F cell combination therapy in other organs, which is difficult to be expected from in vitro experiment alone.

What is claimed is:

1. A method for treating solid tumor cancer, consisting of:

(i) introducing cytosine deaminase (CD) into a mesenchymal stem cells (MSC) to prepare mesenchymal stem cell/cytosine deaminase (MSC/CD) cells;

(ii) freezing the prepared MSC/CD cells and thawing immediately after freezing, followed by centrifugation and removing a supernatant produced by the centrifugation, wherein the thawed cells have not undergone an additional culturing, to prepare F cells;

(iii) administering, via injection directly into the tumor, the F cells to a subject having solid tumor cancer in need of treatment;

(iv) administering 5-fluorocytosine (5-FC) for one week to the subject in need of treatment; and (v) administering an anti-cancer agent other than 5-fluorocytosine following the completing of administering 5-fluorocytosine to the subject in need of treatment.

2. The method according to claim 1, wherein the anticancer agent of (v) is at least one selected from the group consisting of nitrogen mustard, imatinib, oxaliplatin, rituximab, elotinib, trastuzumab, gefitinib, bortezomib, sunitinib, carboplatin, sorafenib, bevacizumab, cetuximab, viscum album, asparaginase, tretinoin, hydroxycarbamide, dasatinib, estramustine, gemtuzumab ozogamicin, ibritumomab tiuxetan, heptaplatin, methylaminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacytidine, cytarabine, fludarabine, enocitabine, decitabine, mercaptopurine, thioguanine, cladribine, carmofur, raltitrexed, docetaxel, paclitaxel, belotecan, topotecan, vinorelbine, etoposide, vincristine, vinblastine, tenifocide, idarubicin, epirubicin, mitoxantrone, mitomycin, bleomycin, daunorubicin, dactinomycin, pirarubicin, aclarubicin, pepromycin, temozolomide, busulfan, ifosfamide, cyclophosphamide, melphalan, altretamine, dacarbazine, thiotepa, nimustine, chlorambucil, mitolactol, taxotere, gleevec, taxol, herceptin, tarceva, avastin, zoladex, adriamycin, irinotecan, 10058-F4, cisplatin, cyclophosphamid, nitrosourea-based anti-cancer agent, methotrexate, carmustine (BCNU), lomustine (CCNU), and doxorubicin.

3. The method according to claim 1, wherein the F cells of step (iii) and the 5-fluorocytosine of step (iv) are administered simultaneously or sequentially.

4. The method according to claim 1, wherein the administration of the F cells according to step (iii) is repeated with a cycle of 10 to 30 days.

5. The method according to claim 1, wherein the cancer is at least one selected from the group consisting of squamous cell cancer, small cell lung cancer, non-small cell lung cancer, lung cancer, peritoneal cancer, colorectal cancer, biliary tumor, nasopharyngeal cancer, laryngeal cancer, bronchial cancer, oral cancer, osteosarcoma, gallbladder cancer, kidney cancer, leukemia, bladder cancer, melanoma, brain cancer, glioma, brain tumor, skin cancer, pancreatic cancer, breast cancer, liver cancer, bone cancer, esophageal cancer, colon cancer, gastric cancer, cervical cancer, prostate cancer, ovarian cancer, head and neck cancer, and rectal cancer.

6. The method according to claim 1, in which the F cells and the 5-fluorocytosine are administered by injection into a cancer tumor in a tissue or organ of the subject.

7. The method according to claim 1, in which the F cells, the 5-fluorocytosine, and the anti-cancer agent other than 5-fluorocytosine are administered by injection into a cancer tumor in a tissue or organ of the subject.

8. The method according to claim 7, comprising a cycle of repeated administration of the F cells, the 5-fluorocytosine, and the anti-cancer agent other than 5-fluorocytosine.

9. The method according to claim 8, wherein the cycle comprises repeated administration every 10 to 30 days.

* * * * *